United States Patent
Keshet et al.

(10) Patent No.: US 11,207,055 B2
(45) Date of Patent: Dec. 28, 2021

(54) ULTRASOUND CARDIAC DOPPLER STUDY AUTOMATION

(71) Applicant: General Electric Company, Schenectady, NY (US)

(72) Inventors: Renato Keshet, Haifa (IL); Omer Barkol, Haifa (IL); Eyal Hayun, Haifa (IL); Eigil Samset, Oslo (NO); Elina Sokulin, Tirat Carmel (IL)

(73) Assignee: General Electric Company, Schenectady, NY (US)

(*) Notice: Subject to any disclaimer, the term of this patent is extended or adjusted under 35 U.S.C. 154(b) by 573 days.

(21) Appl. No.: 16/154,202

(22) Filed: Oct. 8, 2018

(65) Prior Publication Data

US 2020/0107818 A1    Apr. 9, 2020

(51) Int. Cl.
| | |
|---|---|
| *G06K 9/00* | (2006.01) |
| *A61B 8/08* | (2006.01) |
| *G06T 7/00* | (2017.01) |
| *A61B 8/06* | (2006.01) |
| *G01S 7/52* | (2006.01) |

(52) U.S. Cl.
CPC ............ *A61B 8/488* (2013.01); *A61B 8/0883* (2013.01); *A61B 8/5246* (2013.01);
(Continued)

(58) Field of Classification Search
CPC ......... A61B 8/06; A61B 8/0883; A61B 8/488; A61B 8/5246; A61B 8/5207;
(Continued)

(56) References Cited

U.S. PATENT DOCUMENTS 5,935,074 A    8/1999   Mo et al.
6,050,948 A    4/2000   Sasaki et al.
(Continued)

FOREIGN PATENT DOCUMENTS

WO    2017058478    4/2017

OTHER PUBLICATIONS

J. Y. David, et al., "Modern spectral analysis techniques for blood flow velocity and spectral measurements with pulsed doppler ultrasound," IEEE Transactions on Biomedical Engineering, No. 38, pp. 589-596, 1991, Abstract only, 2 pages.
(Continued)

*Primary Examiner* — Tom Y Lu
(74) *Attorney, Agent, or Firm* — Hanley, Flight & Zimmerman, LLC

(57) ABSTRACT

Example apparatus, systems, and methods for image data processing are disclosed and described. An example system includes an image capturer to facilitate capture of an image. The example system includes a Doppler spectrum recorder to record a Doppler spectrum. The example system includes a study type inferrer to infer a study type associated with the Doppler spectrum by: processing the Doppler spectrum using at least one neural network to generate a first probability distribution among study type classifications; processing the image using the at least one neural network to generate a second probability distribution among the study type classifications; and combining the first probability distribution and the second probability distribution to infer a study type.

24 Claims, 22 Drawing Sheets

(52) U.S. Cl.
CPC .............. *G06T 7/0012* (2013.01); *A61B 8/06* (2013.01); *A61B 8/5207* (2013.01); *A61B 8/5223* (2013.01); *G01S 7/52071* (2013.01); *G06T 2207/10132* (2013.01); *G06T 2207/20056* (2013.01); *G06T 2207/20076* (2013.01); *G06T 2207/20081* (2013.01); *G06T 2207/30048* (2013.01)

(58) Field of Classification Search
CPC ................. A61B 8/5223; G01N 15/06; G01N 2015/0046; G01N 2015/0693; G01N 21/274; G01N 21/3504; G01N 21/534; G01R 31/2829; G01S 15/8979; G01S 7/52071; G01S 7/52098; G06T 2207/10132; G06T 2207/20056; G06T 2207/20076; G06T 2207/20081; G06T 2207/30048; G06T 7/0012
See application file for complete search history.

(56) References Cited

U.S. PATENT DOCUMENTS

| | | | | |
|---|---|---|---|---|
| 7,244,230 | B2 * | 7/2007 | Duggirala | A61B 8/00 600/300 |
| 7,678,050 | B2 | 3/2010 | Aase et al. | |
| 10,206,651 | B2 * | 2/2019 | Sokulin | A61B 8/5223 |
| 2007/0161898 | A1 * | 7/2007 | Hao | A61B 8/488 600/443 |
| 2014/0303499 | A1 * | 10/2014 | Toma | A61B 8/488 600/454 |
| 2019/0099161 | A1 * | 4/2019 | Faraggi | G06T 7/11 |

OTHER PUBLICATIONS

F. Marzbanrad, et al., "Automated estimation of fetal cardiac timing events from doppler ultrasound signal using hybrid models," IEEE Journal of Biomedical and Health Informatics, No. 4, pp. 1169-1177, 2014, 9 pages.

J. H. Park, et al., "Automatic cardiac view classification of echocardiogram," IN 2007 IEEE 11th International Conference on Computer Vision, 2007, 8 pages.

G. N. Balaji, et al., "Automatic classification of cardiac views in echocardiogram using histogram and statistical features," Procedia Computer Science, No. 46, pp. 1569-1576, 2015.

H. Khamis, et al., "Automatic apical view classification of echocardiograms using a discriminative learning dictionary," Medical Image Analysis, No. 36, pp. 15-21, 2017, Abstract, 2 pages.

Wikipedia, "Fast Fourier Transform," available at [https://en.wikipedia.org/wiki/Fast_Fourier_transform], 12 pages.

* cited by examiner

| Predicted \ Actual | AR | AVO | LVOT | MR | MVI | PVO | Pulm Vein | RVOT | TR | TVI | LAT | RV | SEPT |
|---|---|---|---|---|---|---|---|---|---|---|---|---|---|
| AR | 14 | | | | | | | | 1 | | | | |
| AVO | | 60 | 4 | 1 | | | | | 3 | | | | |
| LVOT | | | 41 | 1 | | | | | | | | | |
| MR | | 2 | 15 | | | | | | | | | | |
| MVI | | | 3 | 79 | | | | | | | | | |
| PVO | 1 | | | | 26 | | | | | | | | |
| Pulm Vein | | | | | 34 | | | | | | | | |
| RVOT | | | | | | 30 | | | | | | | |
| TR | | 2 | | 2 | | | | 48 | | | | | |
| TVI | | | | | | | | | 25 | | | | |
| LAT | | | | | | | | | | 48 | | | |
| RV | | | | | | | | | | 2 | 20 | | |
| SEPT | | | | | | | | | | | 1 | 1 | 20 |

FIG. 15

ULTRASOUND CARDIAC DOPPLER STUDY AUTOMATION

FIELD OF THE DISCLOSURE

This disclosure relates generally to improved imaging systems and, more particularly, to improved machine learning systems and methods for medical image processing.

BACKGROUND

A Cardiac Doppler ultrasound study enables the analysis of blood flow through the heart, which can help physicians assess heart function (including systolic and/or diastolic function) and/or discover vascular obstructions in a non-invasive way. As opposed to a B-Mode tissue ultrasound scan, in which a sequence of two-dimensional images is obtained, a Doppler scan can provide information for a particular point or beam direction. A Doppler scan output is a spectrum of movement velocities through the point and/or direction of interest. Currently, Doppler scan processing cannot be automated because systems are not able to identify a type of Doppler study to determine how to process acquired Doppler data.

BRIEF DESCRIPTION

Certain examples provide systems and methods for improved image data processing.

Certain examples provide a Doppler study classification system including an image capturer to facilitate capture of at least one of a two-dimensional ultrasound image or a B-Mode image of a target. The example system includes a Doppler spectrum recorder to record a captured Doppler spectrum of the target. The example system includes a study type inferrer to infer a study type associated with the Doppler spectrum by at least: processing the Doppler spectrum using at least one neural network to generate a first probability distribution among a plurality of study type classifications; processing the at least one of the two-dimensional ultrasound image or the B-Mode image using the at least one neural network to generate a second probability distribution among a plurality of study type classifications; and combining the first probability distribution of study type classifications and the second probability distribution of study type classifications to infer the study type.

Certain examples provide a computer-readable storage medium including instructions which, when executed, cause at least one processor to at least: process a scanned Doppler spectrum using at least one neural network to generate a first probability distribution among a plurality of study type classifications; process at least one of the two-dimensional ultrasound image or the B-Mode image using the at least one neural network to generate a second probability distribution among a plurality of study type classifications; and combine the first probability distribution of study type classifications and the second probability distribution of study type classifications to infer a study type associated with a Doppler scan.

Certain examples provide a computer-implemented method including: processing, using at least one processor, a scanned Doppler spectrum using at least one neural network to generate a first probability distribution among a plurality of study type classifications; processing, using the at least one processor, at least one of the two-dimensional ultrasound image or the B-Mode image using the at least one neural network to generate a second probability distribution among a plurality of study type classifications; and combining, using the at least one processor, the first probability distribution of study type classifications and the second probability distribution of study type classifications to infer a study type associated with the scanned Doppler spectrum.

BRIEF DESCRIPTION OF THE DRAWINGS

FIG. 15 shows a table of example Doppler study classification results.

The figures are not scale. Wherever possible, the same reference numbers will be used throughout the drawings and accompanying written description to refer to the same or like parts.

DETAILED DESCRIPTION

Figure 1:
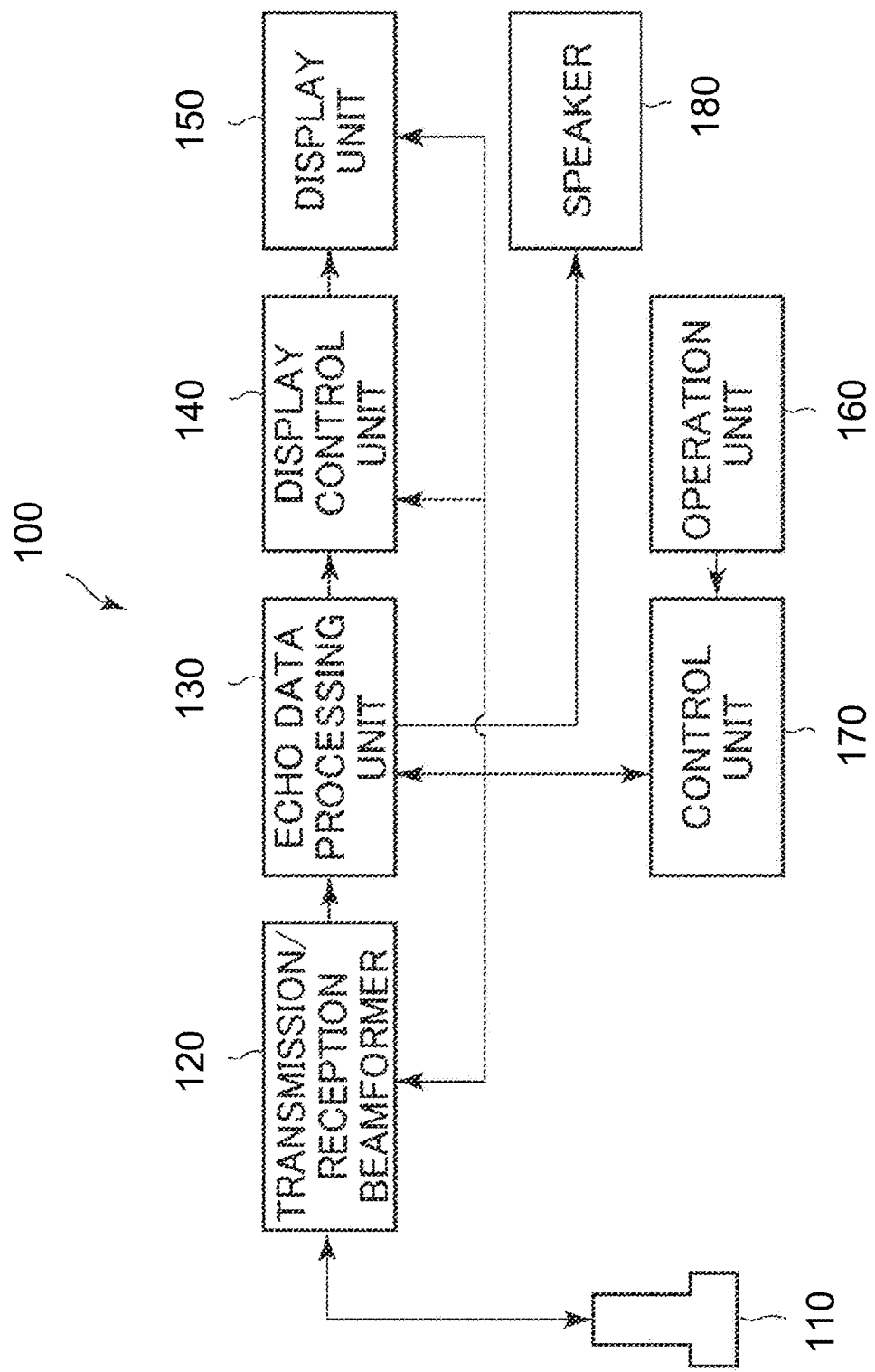
FIGS. 1-2 illustrate an example imaging system to which the methods, apparatus, and articles of manufacture disclosed herein can be applied.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. Overview

Imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

An alternative to a convolutional neural network is a fully-connected neural network. A fully-connected neural network includes hidden layers in which every node is connected to every other node in the next layer. Conversely, a sparse-layered neural network includes hidden layers that are connected to only a few inputs and a few outputs. In a fully-connected neural network, each node or neuron in a hidden layer receives input from all nodes/neurons in the previous layer of the network, forming dense connections between nodes and layers.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Deep Learning and Other Machine Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. Description of Examples

Example Imaging Systems and Methods

Figure 2:
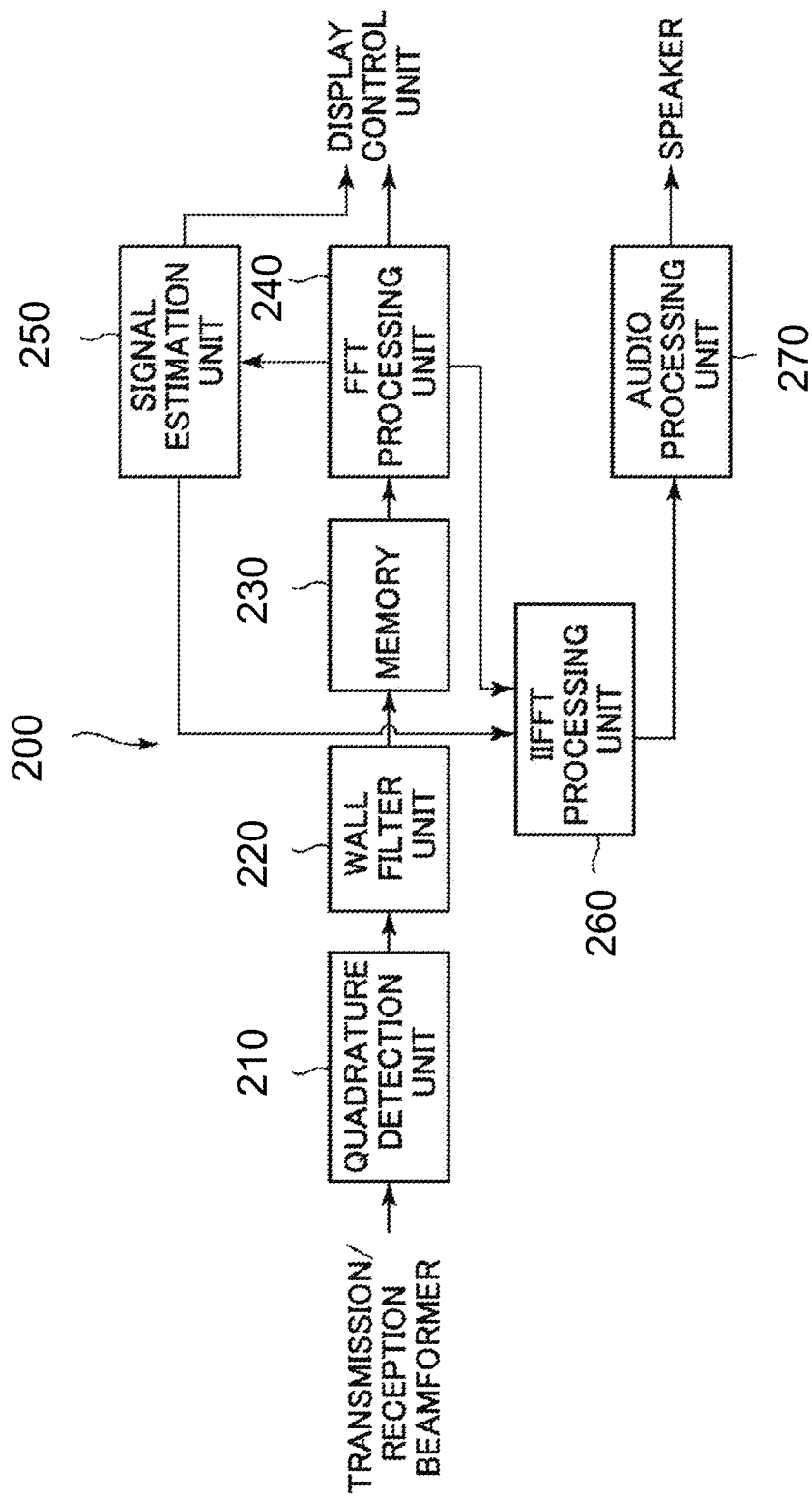

The methods, apparatus, and articles of manufacture described herein can be applied to a variety of healthcare and non-healthcare systems. In one particular example, the methods, apparatus, and articles of manufacture described herein can be applied to the components, configuration, and operation of an ultrasound imaging system. FIGS. 1-2 illustrate an example implementation of an ultrasound imaging scanner apparatus to which the methods, apparatus, and articles of manufacture disclosed herein can be applied.

An example ultrasound diagnostic apparatus 100 is illustrated in FIG. 1. The example apparatus 100 includes an ultrasound probe 110, a transmission/reception beamformer 120, an echo data processing unit 130, a display control unit 140, a display unit 150, an operation unit 160, a control unit 170, and a speaker 180.

The example ultrasound probe 110 includes a plurality of ultrasound transducers (not shown) arranged in an array. The ultrasound transducer array transmits ultrasound waves to a target and receives an echo signal from the target in return. The transmission/reception beamformer 120 supplies an electric signal to the ultrasound probe 110 based on a control signal from the control unit 170 to transmit ultrasound waves from the ultrasound probe 110 using a specified parameter. The transmission/reception beamformer 120 performs signal processes such as amplification, analog-to-digital (A/D) conversion, and phase rectifying addition on an echo signal received at the ultrasound probe 110 using a specified parameter. The transmission/reception beamformer 120 outputs processed echo data to the echo data processing unit 130. The transmission/reception beamformer 120 configures transmission/reception parameters according to an imaging mode such as a B-mode, a Doppler mode, and a color Doppler mode.

In certain examples, the echo data processing unit 130 includes a B-mode processing unit and a Doppler processing unit. In certain examples, the echo data processing unit 130 can also include a color Doppler processing unit. The echo data processing unit 130 generates B-mode data by performing B-mode processing, such as logarithmic compression and envelope detection, on echo data output from the transmission/reception beamformer 120. The color Doppler processing unit generates color Doppler data by performing color Doppler processing such as quadrature detection, Moving Target Indication (MTI) filter processing, and autocorrelation processing, etc. The Doppler processing unit performs Doppler processing on the echo data to acquire a flow velocity spectrum such as a blood flow (e.g., a Doppler processing function).

The display control unit 140 uses a scan converter to convert data output from the echo data processing unit 130 into ultrasound image data by scanning. The display control unit 140 allows the display unit 150 to display an ultrasound image based on the ultrasound image data. The echo data processing unit 130 outputs B-mode data acquired from the B-mode processing unit, Doppler spectrum data acquired from the Doppler processing unit, and color Doppler data acquired from the color Doppler processing unit. The ultrasound image data includes B-mode image data, Doppler image data, and color Doppler image data. The display control unit 140 displays a B-mode image based on B-mode data, a Doppler image based on Doppler spectrum data, and a color Doppler image based on color Doppler data. The example display unit 150 includes a Liquid Crystal Display (LCD) or a Cathode Ray Tube (CRT), for example. The example operation unit 160 includes a keyboard/keypad, a pointing device, and/or other interface for an operator to enter an instruction or information. The example control unit 170 includes a Central Processing Unit (CPU) and/or other processor. The example control unit 170 reads a control program stored in a storage unit and performs functions for the components of the ultrasound diagnostic apparatus 100. The example speaker 180 outputs Doppler sound based on a signal output from the echo data processing unit 130.

FIG. 2 shows an example implementation of the Doppler processing unit 200 of the example echo data processing unit 130. As illustrated in FIG. 2, the Doppler processing unit 200 includes a quadrature detection unit 210, a wall filter unit 220, memory 230, a Fast Fourier Transform (FFT) processing unit 240, a signal estimation unit 250, an Inverse Fast Fourier Transform (IFFT) processing unit 260, and an audio processing unit 270.

In the example of FIG. 2, the transmission/reception beamformer 120 inputs data to the Doppler processing unit 200. For example, the data is first input to the quadrature detection unit 210. The quadrature detection unit 210 performs quadrature detection on the input data. The wall filter unit 220 filters the data to generate Doppler data. The Doppler data output from the wall filter unit 220 is stored in the memory 230.

In certain examples, the memory 230 is implemented as or is equivalent to a sliding ring-buffer. For example, a group of data D1, D2, D3, D4, D5, etc., is read from the memory 230 for FFT processing. The data is then input to the FFT processing unit 240. The FFT processing unit 240 performs FFT processing on data supplied from the memory 230 to generate Doppler spectrum data. If missing part estimation is not performed on the Doppler spectrum data, the FFT processing unit 240 outputs the Doppler spectrum data to the display control unit 140 and the IFFT processing unit 260. If missing part estimation is performed on the Doppler spectrum data, the FFT processing unit 240 outputs the Doppler spectrum data to the signal estimation unit 250. For example, the FFT processing unit 240 separates output of the Doppler spectrum data to the display control unit 140 and the IFFT processing unit 260 from output of the Doppler spectrum data to the signal estimation unit 250.

The signal estimation unit 250 estimates a missing part of the Doppler spectrum data (e.g., using a signal estimation function). A missing part of the Doppler spectrum data can result during a period in which ultrasound transmission/reception in the B-mode or the color Doppler mode is performed and ultrasound transmission/reception in the Doppler mode is not performed. The signal estimation unit 250 uses an extrapolation process to estimate missing part of the Doppler spectrum data, for example. For example, the signal estimation unit 250 performs the extrapolation process based on a temporal change of average frequency in a certain frequency spectrum for the Doppler spectrum data. After being supplemented with the extrapolated estimate of missing information by the signal estimation unit 425, Doppler spectrum data is output to the display control unit 140 and the IFFT processing unit 260.

The display control unit 140 allows the display unit 150 to display a Doppler image generated based on the Doppler spectrum data that is supplied from the signal estimation unit 250 and/or the FFT processing unit 240. The IFFT processing unit 260 performs an IFFT process on the Doppler spectrum data supplied from the signal estimation unit 250 and/or the FFT processing unit 240. The IFFT-processed data is output to the audio processing unit 270. The audio processing unit 270 performs an audio process on the data supplied from the IFFT processing unit 260 and outputs a signal to the speaker 180. The speaker 180 outputs Doppler sound. As described above, the signal estimation unit 250 performs the extrapolation process to supplement a missing part without delay even if the Doppler sound is output based on the Doppler spectrum data output from the signal estimation unit 250. Therefore, the Doppler sound can be output without delay. If the signal estimation unit 250 performs no process, the wall filter unit 220 can supply data to the audio processing unit 270 and output the Doppler sound.

In many examples, a user performs a Doppler scan using the ultrasound scanning apparatus 100 but does not indicate a kind or type of study performed. For example, when a scan is performed by a sonographer and saved for future measurement and diagnosis by a cardiologist, the cardiologist often forgets to configure study type. When the type or kind of imaging study is not indicated by the user, the ultrasound apparatus 100 is unable to perform measurement automation, as the system 100 does not know what measurement is to be taken and with which algorithm.

Cardiac Doppler ultrasound studies enable the analysis of blood flow through the heart, which can help physicians assess the heart's function (e.g., including systolic and/or diastolic function) and/or discover vascular obstructions, in a non-invasive way. Differently from a tissue (B-Mode) ultrasound scan, in which a two-dimensional (2D) sequence of images is obtained, a Doppler scan can provide information for one particular point or beam direction at a time. An output of the Doppler scan is a spectrum of movement velocities through the point/direction of interest.

A user, such as a physician, etc., can decide to perform one or more of a variety of Doppler scan studies, which depend in part on a position of a point and/or an angle of a direction of interest within the heart. Some of the positions/points/locations of interest at which a physician may examine a patient are at different heart valves (e.g., mitral, tricuspid, aortic, etc.), heart tissues (e.g., septal, lateral, anterior and inferior points at the base of the mitral annulus, etc.) arteries/veins (e.g., pulmonary vein, left ventricle output tract, etc.), etc. Directions of interest can pass through these points of interest, for example. The type of Doppler study can also depend on the flow direction of interest. For example, the flow direction of interest can follow physiological blood flow, flow in the abnormal, opposite direction (called "regurgitation"), etc.

Taking the above into consideration, some types of Doppler ultrasound studies include: Aortic Regurgitation (AR), Aortic Valve Out Flow (AVO), Left Ventricle Output Tract (LVOT), Mitral Valve Regurgitation (MR), Mitral Valve In Flow (MVI), Pulmonary Valve Out Flow (PVO), Pulmonary Vein (PulmVein), Right Ventricle Output Tract (RVOT), Lateral Tissue Doppler In Flow (LAT), Septal Tissue Doppler In Flow (SEP), Right Ventricle Tissue Doppler In Flow (RV), Tricuspid Valve Regurgitation (TR), and Tricuspid Valve In Flow (TVI).

A cardiac Doppler ultrasound study often ends by the physician/sonographer performing one or more measurements on the Doppler scanned spectrum. The measurement(s) include a visual selection of a clinically relevant measurement and the measurement itself, which typically involves manual velocity peaks/slopes detection and/or velocity envelope tracing, for example.

Certain examples provide ultrasound imaging systems (e.g., cardiovascular ultrasound imaging systems) and associated algorithms to perform some or all of the above measurements automatically. For example, the GE Vivid S70™, Vivid E95™, and Vivid IQ™ ultrasound systems provide automatic tracing capabilities, as well as detection of E-wave and A-wave peak velocity detection and E-wave deceleration slope extraction. The clinically relevant measurement, as well as the automation algorithm, are dependent on which type of Doppler study (as listed above) is conducted. For MVI, for example, the physician is often interested in E/A peak ratio (e.g., used in diagnosis of diastolic dysfunction and other pathologies). For LVOT, however, the area under an envelope trace (e.g., for computation of cardiac output) is of interest, for example.

Example Learning Network Systems

Figure 3:
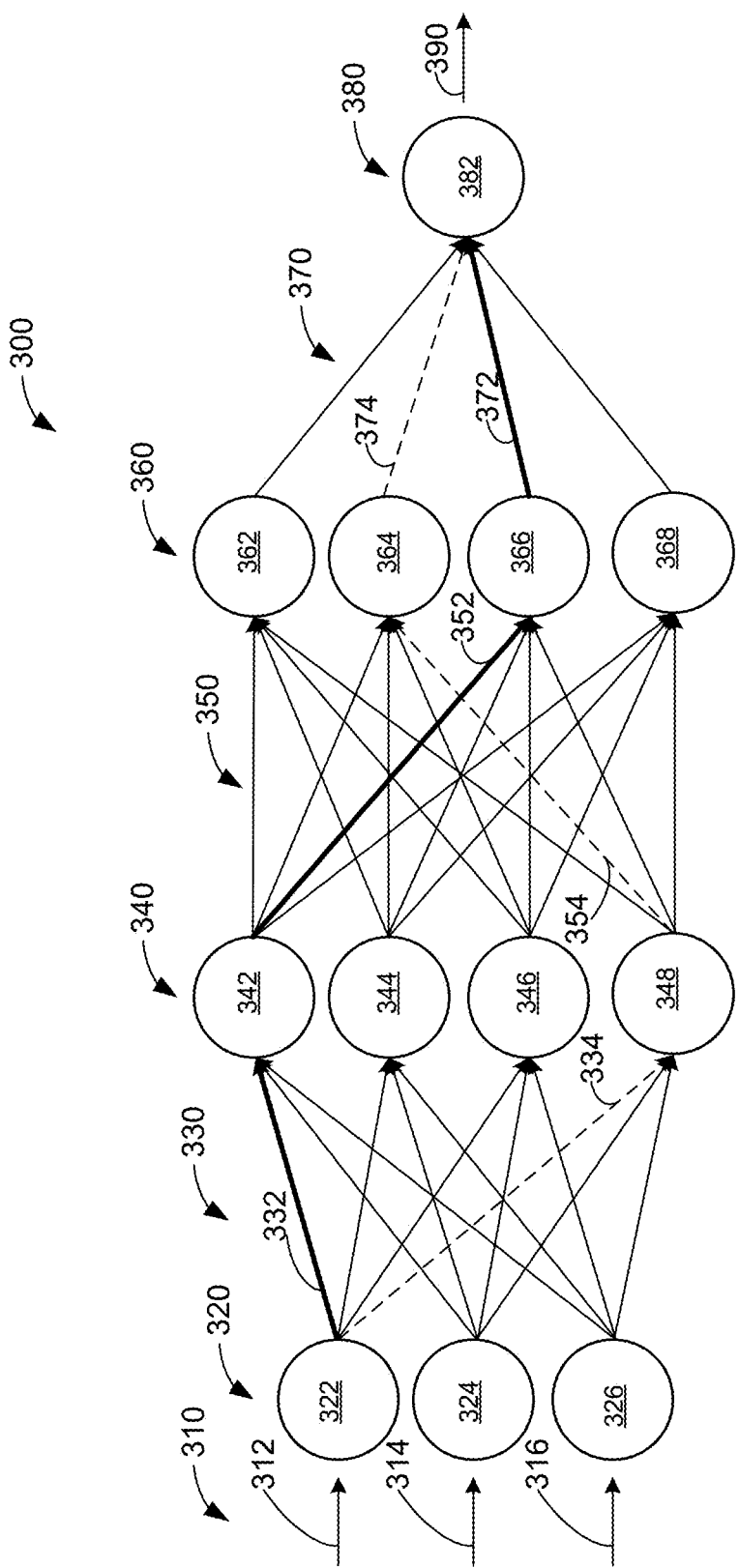
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
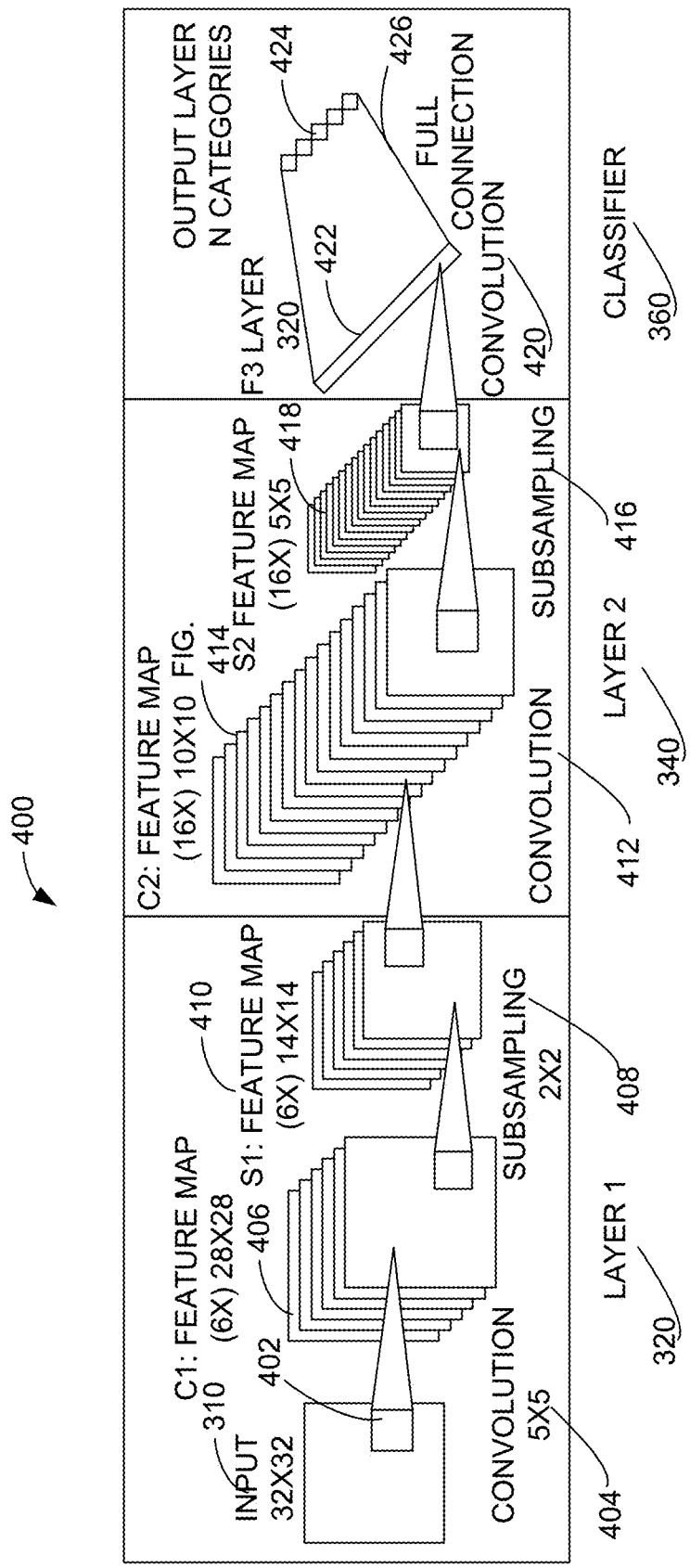
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

In other examples, an alternative to a convolutional neural network, such as a fully-connected neural network, etc., can be employed to extract features and/or quantify metrics. In a fully-connected neural network, all inputs of the layers of the network are mapped to all of the outputs of the respective layer. In contrast, a convolutional layer of a CNN maps only a moving window to the output.

Figure 5:
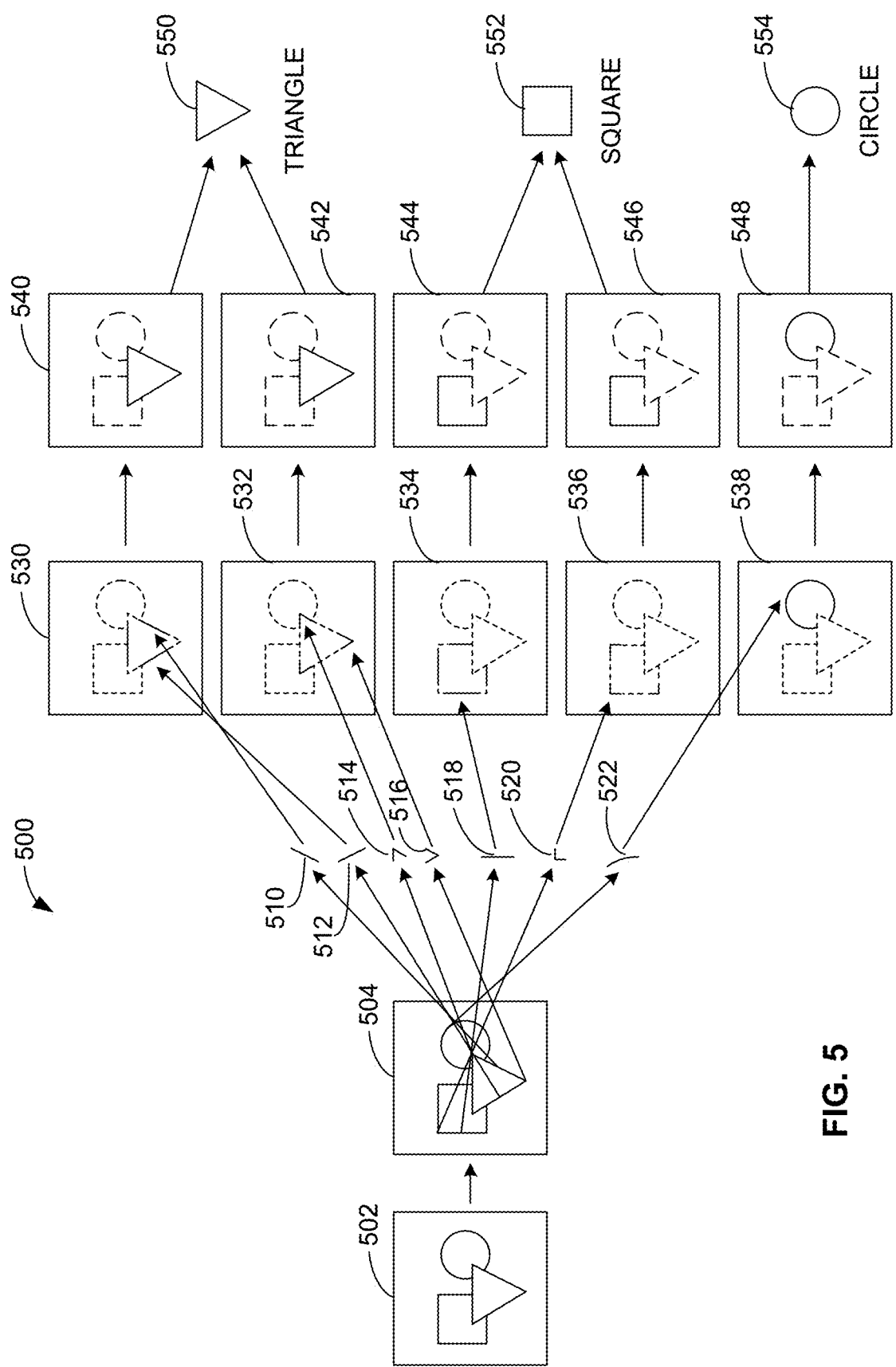
FIG. 5 is a representation of an example implementation of a neural network.

FIG. 5 is a representation of an example implementation of a neural network 500. The neural network 500 receives an input image and/or non-image parameters forming one or more matrices 502 (e.g., image pixels and/or coefficients combined with device parameters, etc.) and abstracts the matrices in a layer 504 to identify learned features 510-522. In a second layer 530, the matrices are transformed into a plurality of images 530-538 in which the learned features 510-522 are each accentuated in a respective sub-image 530-538. The matrices 530-538 are further processed to focus on the features of interest 510-522 in the matrices 540-548. The resulting matrices 540-548 are then processed through a layer which reduces the size of the matrices 540-548 to isolate portions 550-554 of the matrices 540-548 including the features of interest 510-522. Outputs 550-554 of the neural network 500 receive values from the last non-output layer and classify the matrices based on the data received from the last non-output layer. In certain examples, the neural network 500 may contain many different variations of layers, learned features, and outputs, etc.

Figure 6A:
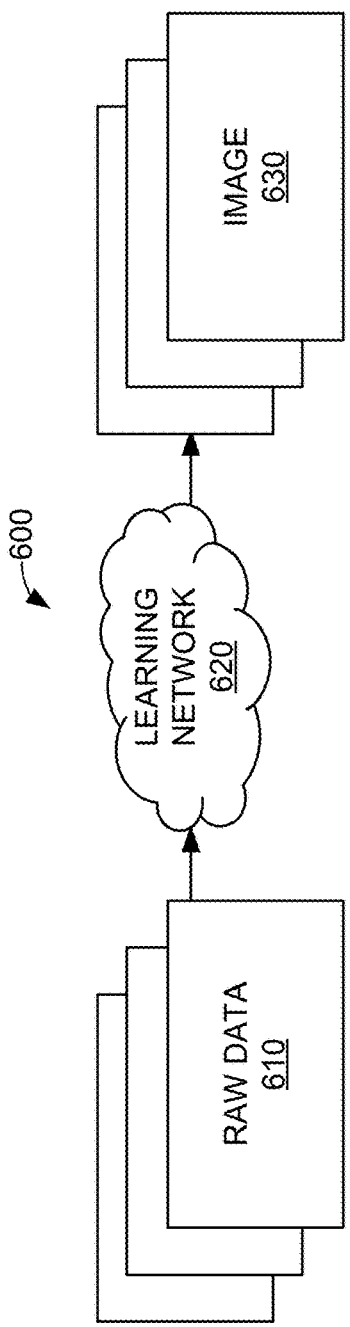
FIG. 6A illustrates an example configuration to apply a learning network to process and/or otherwise evaluate an image.
Figure 6B:
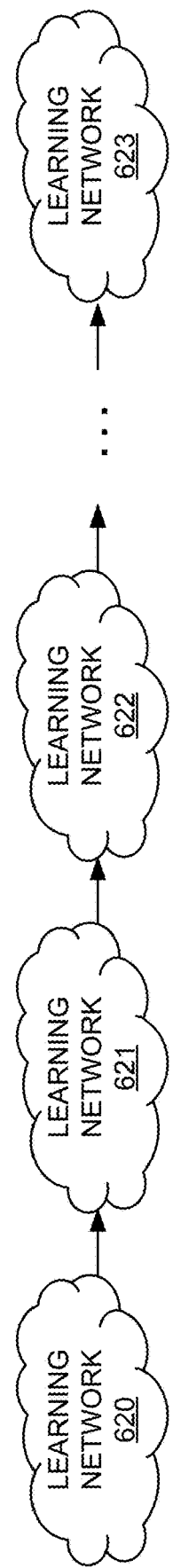
FIG. 6B illustrates a combination of a plurality of learning networks.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620.

Figure 7:
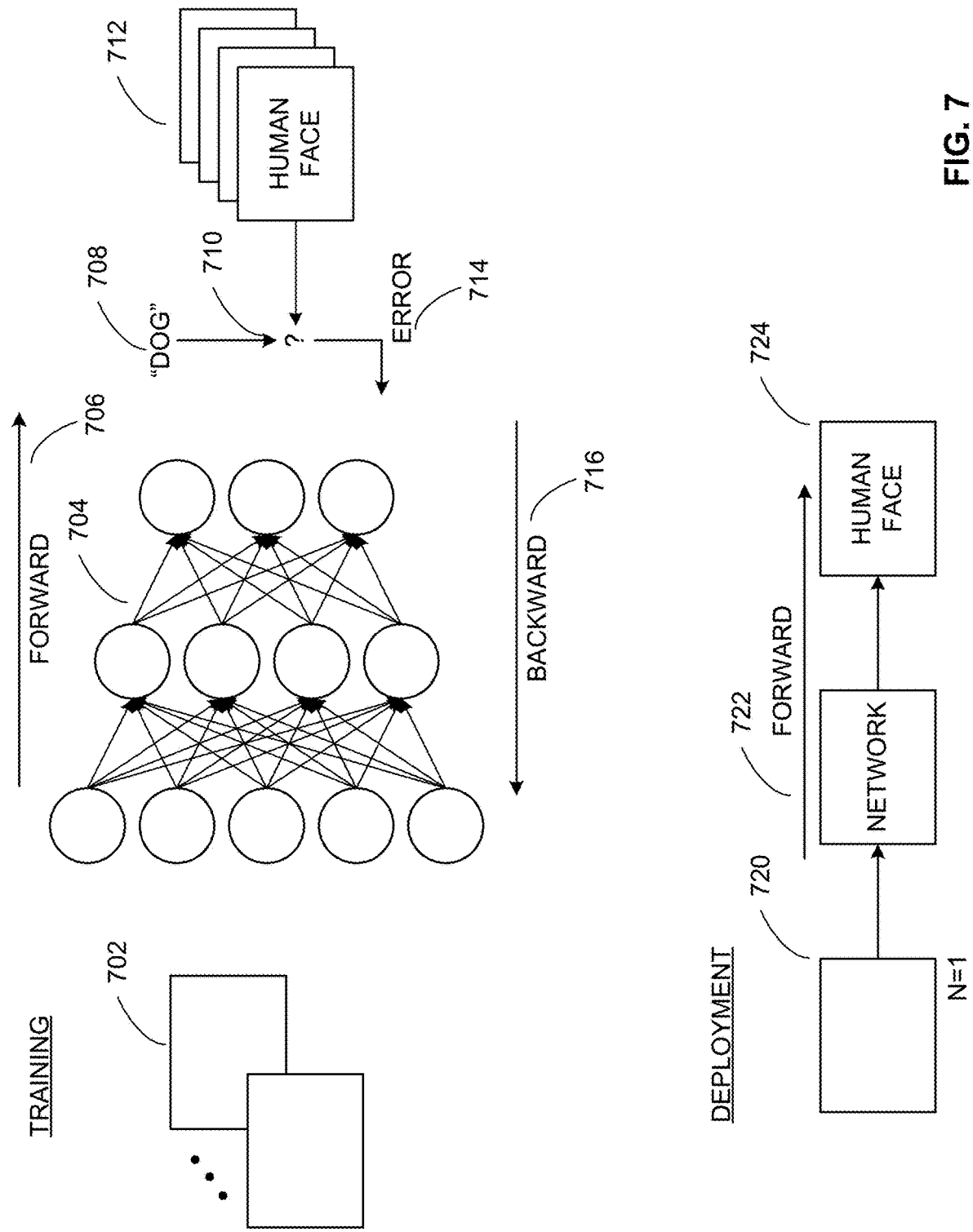
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a dog 708. In training, the network result 708 is compared 710 to a known outcome 712. In this example, the known outcome 712 is a human face (e.g., the input data set 702 represents a human face, not a dog face). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a human face 724.

Figure 8:
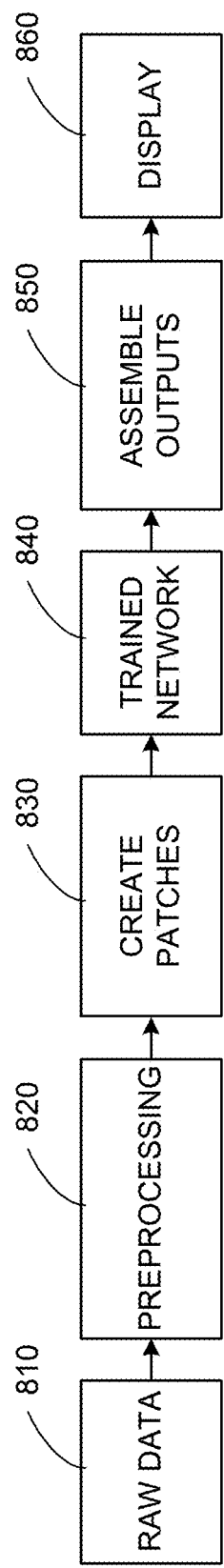
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
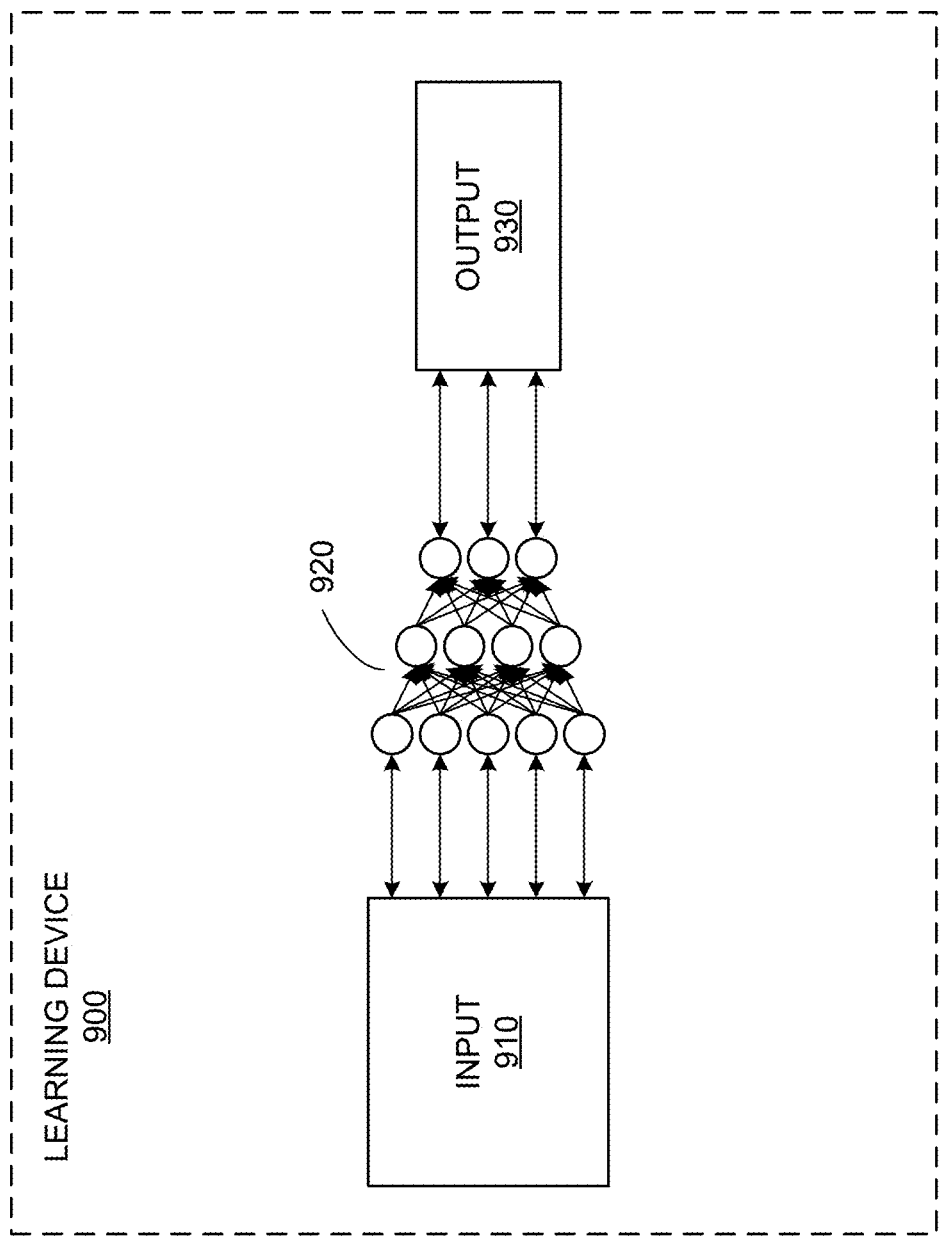
FIGS. 9A-9C illustrate various deep learning device configurations.
Figure 9B:
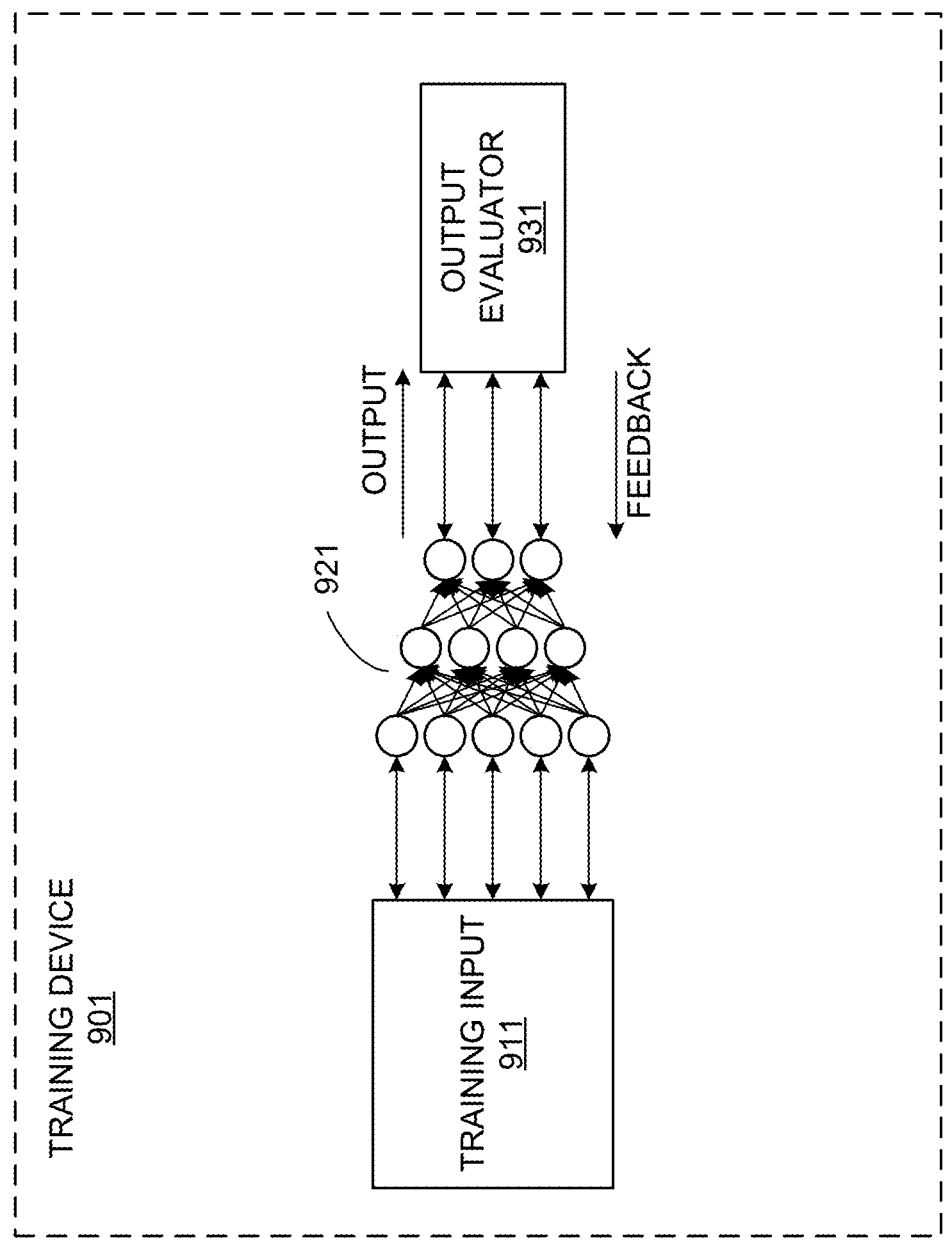
Figure 9C:
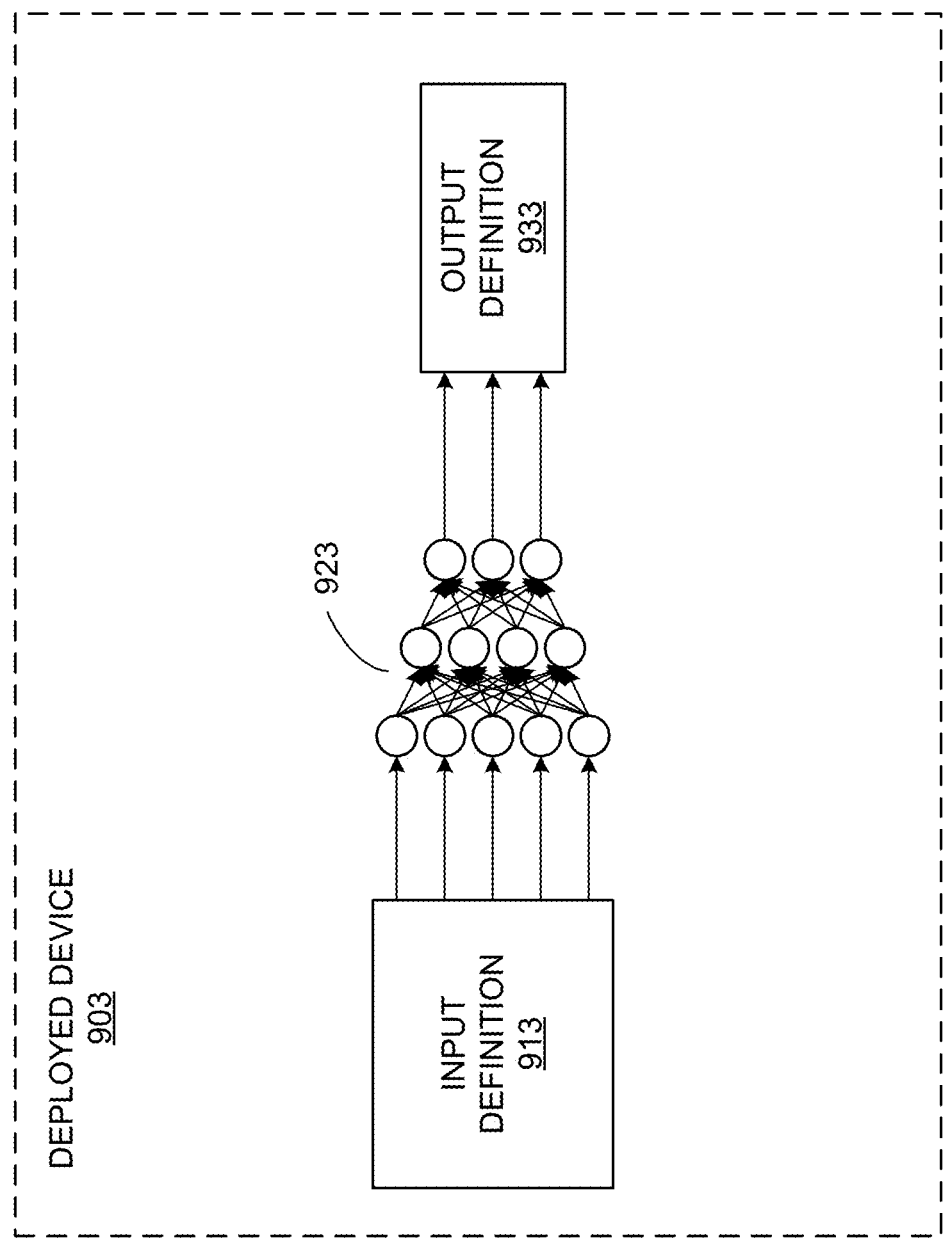

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definitions 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Ultrasound Imaging Systems and Methods

Figure 10A:
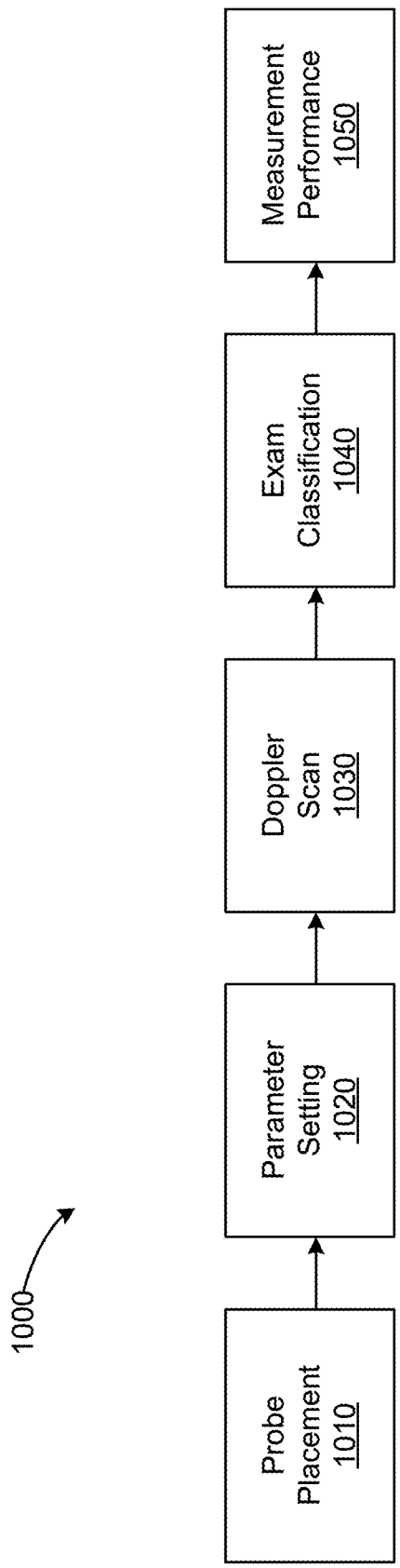
FIG. 10A illustrates an example ultrasound imaging automation process.

FIG. 10A illustrates an example ultrasound imaging automation pipeline or process 1000. The example pipeline 1000 includes probe placement 1010, parameter setting 1020, Doppler scan 1030, exam classification 1040, and measurement performance 1050. At block 1010, placement of an ultrasound probe is determined. For example, probe position dictates an angle of incidence of ultrasound waves produced by the probe on the target anatomy.

For example, if the angle of incidence is perpendicular, or close to perpendicular, more ultrasound waves will be reflected back to the transducer and fewer waves will be "scattered" away, resulting in a better-quality image. However, if the ultrasound waves are more parallel to the surface of the target (e.g., more than a 45° angle of incidence), the image will have less definition. An operator can improve the image of the target by tilting or rotating the probe, thus adjusting the angle of incidence.

Parameter setting 1020 sets and/or otherwise configures ultrasound imaging parameters such as frequency (e.g., high frequency (10-15 MHz), midrange frequency (5-10 MHz), low frequency (2-5 MHz), etc.), gain, mode (e.g., nerve, angio, general, focus, etc.), depth setting, etc., to drive ultrasound system configuration and operation and ultrasound image data acquisition, for example. For example, a heart view can be selected, such as an Apical 2-chamber, 4-chamber, 5-chamber, long axis (APLAX) view, etc. Once the view is selected, a point of interest (referred to as a "Doppler gate position") is selected. Typical gate positions include the different heart valves and specific tissue positions. In addition, an ultrasound mode can be selected, such as continuous wave (CW), pulse wave (PW), or a special mode for tissue Doppler scans (TDI). Additional parameters, as gain, depth, baseline display, etc., can also be set.

The Doppler scan 1030 generates ultrasound waves according to the set parameters 1020 and captures a Doppler spectrum echo produced in response to the incident waves.

For example, once parameters have been set for an ultrasound scan, a patient can be scanned in a tissue mode (referred to as a "B-Mode"), in which the heart's anatomy can be seen on the ultrasound imaging device's screen. Then, a cursor and/or other indicator (referred to as a "gate") is placed on a selected anatomy (gate position). Then, the actual Doppler scan is initiated using the selected ultrasound mode and associated parameters. An output of a Doppler ultrasound scan is typically a spectrogram, which includes a 2D image in which an x axis represents time and a y axis correspond to velocity. Each column of the Doppler spectrogram represents a velocity distribution (histogram) for that particular time. The velocity here refers to a speed of blood flow through the gate position (and/or positions along the gate direction line, in the case of CW), for example. The scanning process is terminated after a time interval (e.g., a few seconds), when the captured spectrum contains the desired information and is of desired quality. At that point, for example, a user and/or automated program presses "freeze" to terminate the scan.

Exam classification 1040 identifies a type of study/exam/scan conducted in the Doppler scan 1030. In certain examples, the exam classification 1040 is determined automatically to drive proper analysis of the captured Doppler spectrum data. Without proper identification of exam type, the resulting exam Doppler information cannot be properly processed and accurately interpreted.

In certain examples, study classification 1040 is executed after the Doppler scan 1030 has been performed. The automatic Doppler study classification module 1030 includes a plurality of neural networks, which have been trained with a plurality (e.g., hundreds, thousands, etc.) of tagged Doppler studies. In some examples, eighty percent of the tagged Doppler study data is used to train the neural networks, and the remaining twenty percent is used to validate the trained networks (e.g., with a 94.85% accuracy, etc.).

Thus, rather than relying on a user to manually indicate (e.g., using menu navigation) the type of Doppler study that is being performed, the system automatically determines the type of study (e.g., AR, AVO, LVOT, MR, MVI, PVO, PulmVein, RVOT, LAT, SEP, RV, TR, TVI, etc.) and a corresponding algorithm to apply to perform performance measurement 1050 automatically. The system determines study type based on a machine learning model processing the obtained Doppler spectrum data and additional information stored in the system before and during the ultrasound scan operation, for example.

Figure 10B:
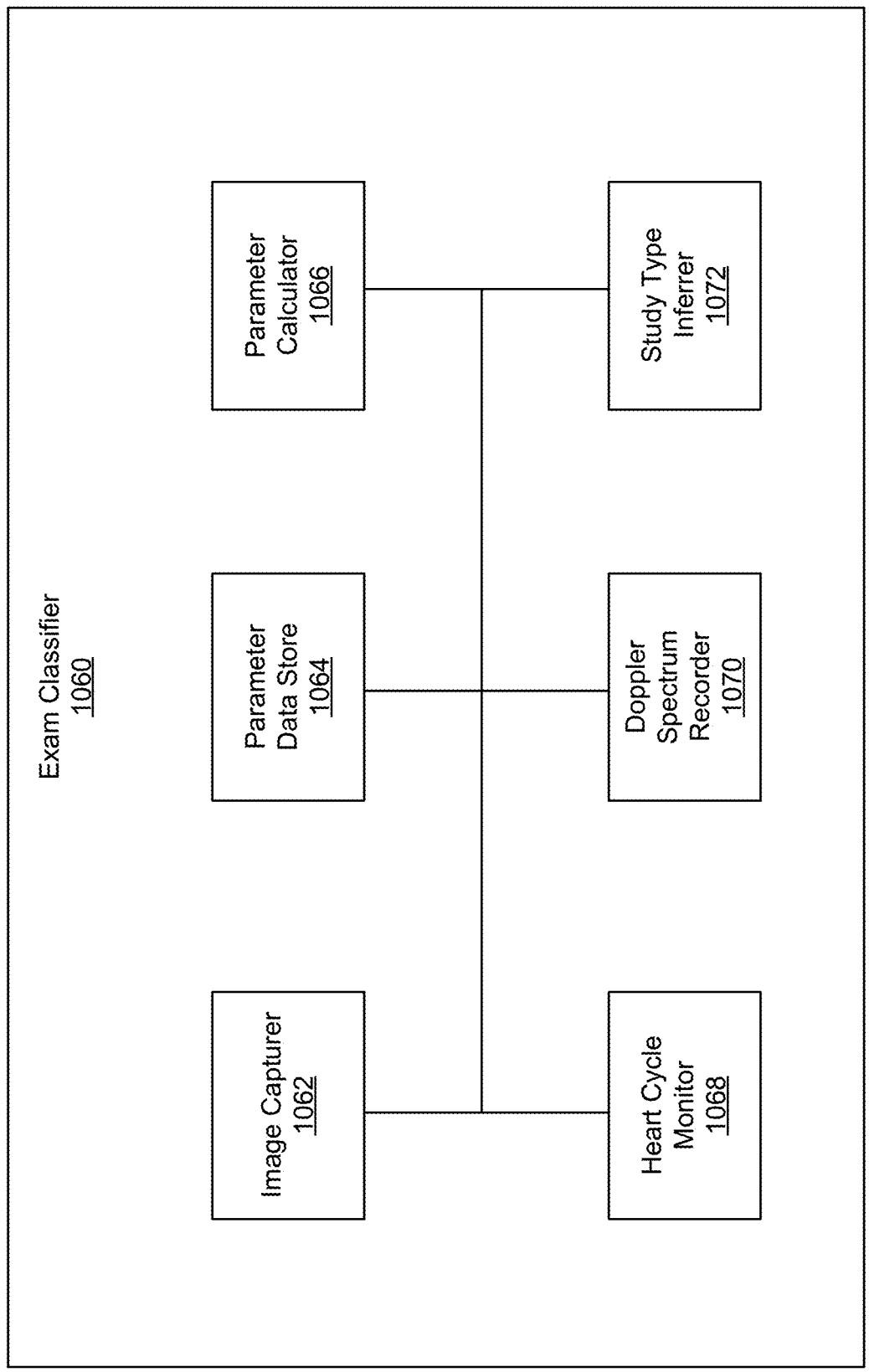
FIG. 10B illustrates an example implementation of an exam classifier.

FIG. 10B illustrates an example implementation of an exam classifier 1060. The example exam classifier 1060 can be implemented as part of the control unit 170 of the example ultrasound system 100 of FIG. 1, for example, to infer exam type to properly process Doppler scan data. While the example control unit 170 can execute instructions to control the entire process 1000 of FIG. 10A, the focus of the illustration of FIG. 10B is on the exam classifier 1060 to execute the exam classification 1040 of the process 1000.

The example exam classifier 1060 includes an image capturer 1062, a parameter data store 1064, a parameter calculator 1066, a heart cycle monitor 1068, a Doppler spectrum recorder 1070, and a study type inferrer 1072. The example image capturer 1062 triggers and/or otherwise facilitates capture of image data (e.g., 2D image data, B-Mode image data, etc.) by the ultrasound system 100. The example parameter data store 1064 stores image scan parameters related to physical scan procedure, device operation, viewing options, storage options, etc. Example scan parameters include scan depth, focus tilt, focus depth, aperture, baseline position, velocity interval, ultrasound mode, etc. The parameter calculator 1066 calculates parameters such as gate coordinates (x,y) indicating an anatomical position of a B-Mode image, etc. The heart cycle monitor 1068 monitors patient heart cycle information. The Doppler spectrum recorder 1070 records captured Doppler spectrum, which can be segmented according to heart cycles from the heart cycle monitor. The study type inferrer 1072 uses the captured image data, parameters, and recorded Doppler spectrum, as segmented according to heart cycle, to infer a study type or classification for the exam being/to be performed. The study type inferrer 1072 can include a plurality of neural networks, filters, and processor(s) to process the available information to infer associated study type. Once a study type has been determined, one or more algorithms corresponding to the study type can be properly applied to process the acquired image data. Otherwise, an erroneous algorithm may be applied to the image data or no algorithm may be applied at all without knowledge of image study type, etc.

Figure 11:
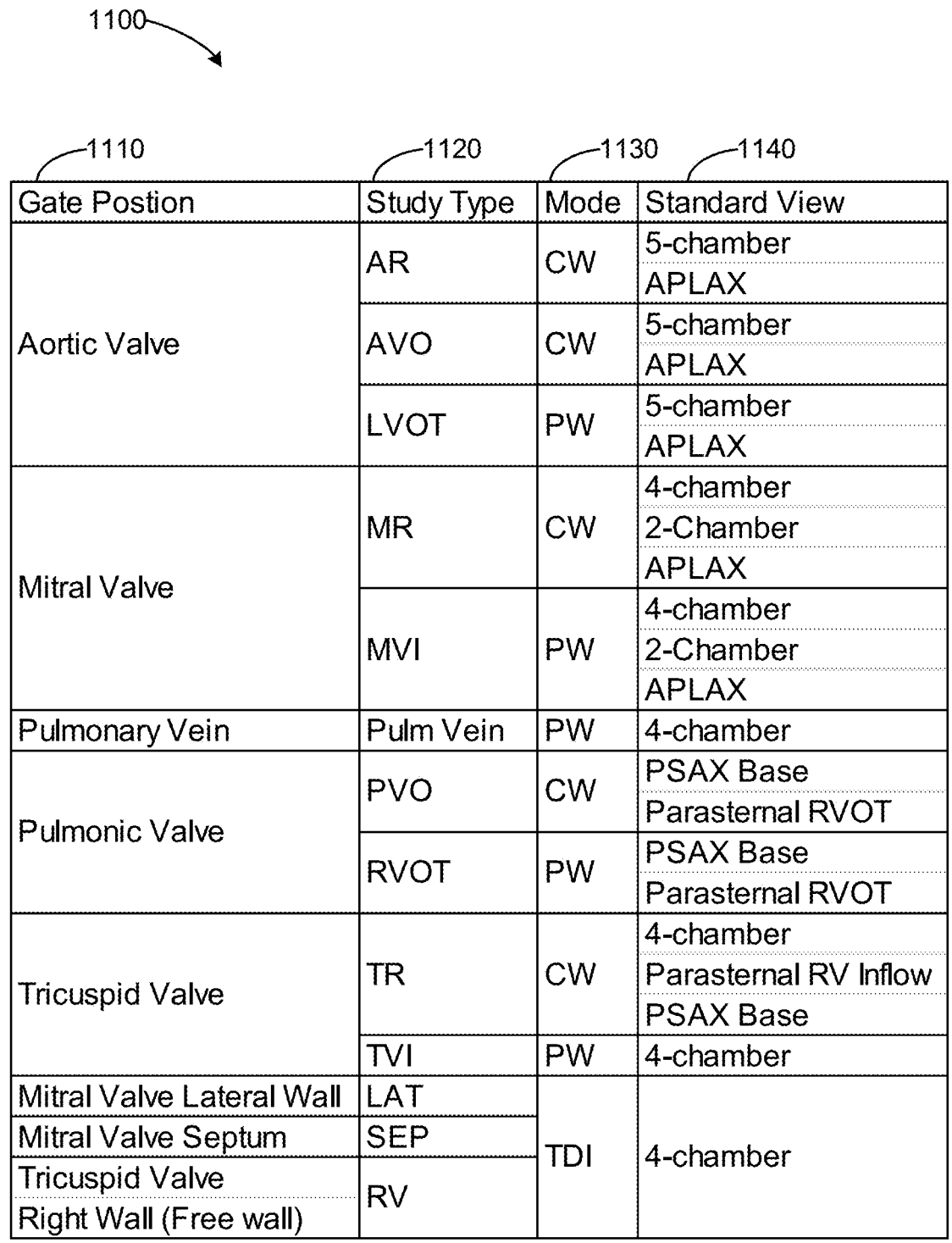
FIG. 11 shows an example relationship between study types and Doppler scan parameters.

FIG. 11 shows an example relationship between study types and Doppler scan parameters. As show in the example table 1100 of FIG. 11, a gate position 1110 is associated with one or more particular study type(s) 1120, imaging mode(s) 1130, and view(s) 1140. For example, when the gate position 1110 is at the aortic valve, the study type 1120 can be any of AR, AVO, or LVOT, for example. The mode 1130 is CW or PW, and the standard view 1140 includes a 5-chamber view and an apical long axis (APLAX) view, for example. When the gate position 1110 is the mitral valve, the study type 1120 can be MR or MVI, for example. The mode 1130 is CW or PW, and the standard view 1140 includes a 4-chamber view, a 2-chamber view, and an APLAX view, for example. When the gate position 1110 is the pulmonary vein, the study type 1120 can be pulmonary vein, for example. The mode 1130 is PW, and the standard view 1140 includes a 4-chamber view, for example. When the gate position 1110 is the pulmonic valve, the study type 1120 can be PVO or RVOT, for example. The mode 1130 is CW or PW, and the standard view 1140 includes a parasternal short axis (P SAX) base view and a parasternal RVOT view, for example. When the gate position 1110 is the tricuspid valve, the study type 1120 can be TR or TVI, for example. The mode 1130 is CW or PW, and the standard view 1140 includes a 4-chamber view with TVI/PW and a 4-chamber view, a parasternal RV inflow view, and a PSAX view with TR/CW, for example. When the gate position 1110 is the mitral valve lateral wall, the study type 1120 can be LAT, for example. The mode 1130 is TDI, and the standard view 1140 includes a 4-chamber view, for example. When the gate position 1110 is the mitral valve septum, the study type 1120 can be SEP, for example. The mode 1130 is TDI, and the standard view 1140 includes a 4-chamber view, for example. When the gate position 1110 is the tricuspid valve right wall (free wall), the study type 1120 can be RV, for example. The mode 1130 is TDI, and the standard view 1140 includes a 4-chamber view, for example.

After the scan is acquired, one or more measurements are performed on the obtained spectrum. An example measurement set, often performed on MVI or TDI studies, includes peak velocities on an E-wave and an A-wave. The E-wave relates to early diastolic inflow (when the ventricles relax and create negative pressure that sucks the blood in), and the A-wave relates to later inflow caused by atria contraction. The relationship between the E- and A-wave peaks (called "E/A ratio") is of relevance when diagnosing pathologies such as Diastolic Dysfunction, etc. Also of interest in some situations is the E-wave deceleration, which includes a negative slope of blood velocities after the E-wave peak.

In other types of studies, different types of measurement are performed. For LVOT, for example, an envelope is estimated, which is a tracing of maximum velocities on the spectrum. Such an envelope is used for assessing, for example, a stroke volume (volume of blood output by the heart per heart cycle), by computing an area below the envelope (e.g., a velocity time integral). Such measurements are traditionally performed manually by a user, which makes the study relatively long and not completely accurate.

However, measurement automation only works if the study type is known. The automation Doppler study classifier 1040 captures and/or otherwise obtains information available at the time of scan completion or "freeze" and returns a study type likely/probabilistically associated with the image acquisition. The study/exam classifier 1040 can include one or more neural networks to automatically classify image study type, which uses tagged traces (e.g., physician-tagged traces, etc.) for network training, for example.

Figure 12:
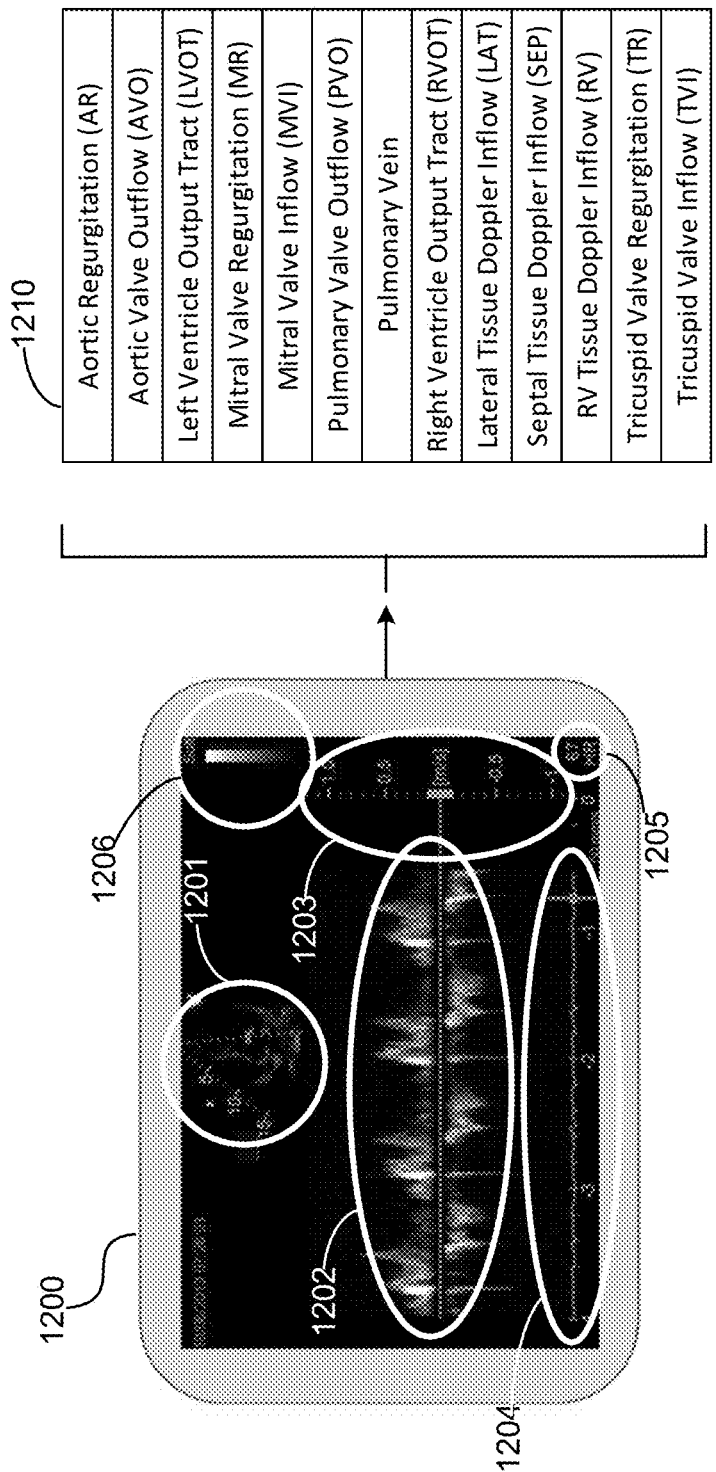
FIG. 12 illustrates an example ultrasound device interface screen.

At "freeze" time, the ultrasound device includes the following data, which can be used for study type classification: a 2D or B-Mode image, scan parameters, and Doppler spectrum heart cycles. FIG. 12 illustrates an example ultrasound device screen 1200 associated with the display unit 150 of the ultrasound imaging device 100. The example interface screen 1200 includes a miniature image 1201 (e.g., an image thumbnail and/or other reduced sized and/or resolution representation of the acquired 2D or B-Mode image. The example interface screen 1200 also includes a captured Doppler spectrum 1202 and associated scale 1203. The example screen 1200 further includes an electrocardiogram (ECG) 1204, heart rate 1205, and a grayscale indicator 1206.

The example of FIG. 12 shows the device screen 1200 in a "freeze" or hold state to capture information used to classify or categorize a type 1210 of study being performed (e.g., AR, AVO, LVOT, MR, MVI, PVO, Pulmonary Vein, RVOT, LAT, SEP, RV, TR, TVI, etc.). The 2D or B-Mode image is an ultrasound frame, scanned in standard B-Mode prior to the Doppler scan. Here, one can see a standard view, as well as the "gate", which points to the area on the anatomy from which the Doppler spectrum was scanned.

In certain examples, hundreds or thousands of scan parameters are stored in the device 1200, relating to a physical scan procedure, to device operation, to view and storage options, etc. In certain examples, a subset of parameters can be selected as indicative of the intended study. One key parameter that is not readily available is the coordinates of the "gate" on the B-Mode image, which can indicate an anatomical position that was scanned. However, gate coordinates (x, y) can be calculated as follows:

$$x = \frac{\langle \text{Focus Depth} \rangle - \langle \text{Min Scan Depth} \rangle}{\langle \text{Max Scan Depth} \rangle - \langle \text{Min Scan Depth} \rangle},$$ (Eq. 1)

$$y = \frac{1}{2} + \frac{\langle \text{Focus Title} \rangle}{\langle \text{Aperture} \rangle}.$$ (Eq. 2)

In certain examples, input parameters include:
1. Scan Depth (dopplerSampleMovie: #UserControls.ROICenter);
2. Focus Tilt (dopplerSampleMovie: #UserControls.BeamPosition), in radians;
3. Max Focus Depth (twoDSampleMovie: #UserControls.DepthEnd);
4. Min Focus Depth (twoDSampleMovie: #UserControls.DepthStart);
5. Aperture (twoDSampleMovie: #UserControls.Width), in radians;
6. Baseline position (metadata: RelativeBaselinePosition);
7. Gate coordinate (x; y), as computed with equations (1) and (2);
8. Velocity Interval (metadata: VelocityInterval), (two values); and
9. Ultrasound Mode (metadata: DopplerModeName).

To convert the Ultrasound Mode string parameter into a useful numerical input, the Ultrasound Mode string is split into three binary indicators {mode_CW, mode_PW, and mode_TDI}, which are actual features used in training and inference.

Using these input parameters, the number of parameter features is thirteen, including six single-valued parameters, two double-valued parameters, and three binary indicators.

In certain examples, a patient is attached to an electrocardiogram (ECG) device during the Doppler scan, and an ECG signal can be captured by the ultrasound device. The ultrasound device uses the ECG signal to compute, for each heart cycle, a trigger at a peak of an ECG R-wave, and the triggers are also stored in the system. The heart cycle triggers can be used to segment a Doppler spectrogram into heart cycle spectrograms. In certain examples, only full heart cycles are considered, and initial and final partial cycles can be discarded.

Figure 13:
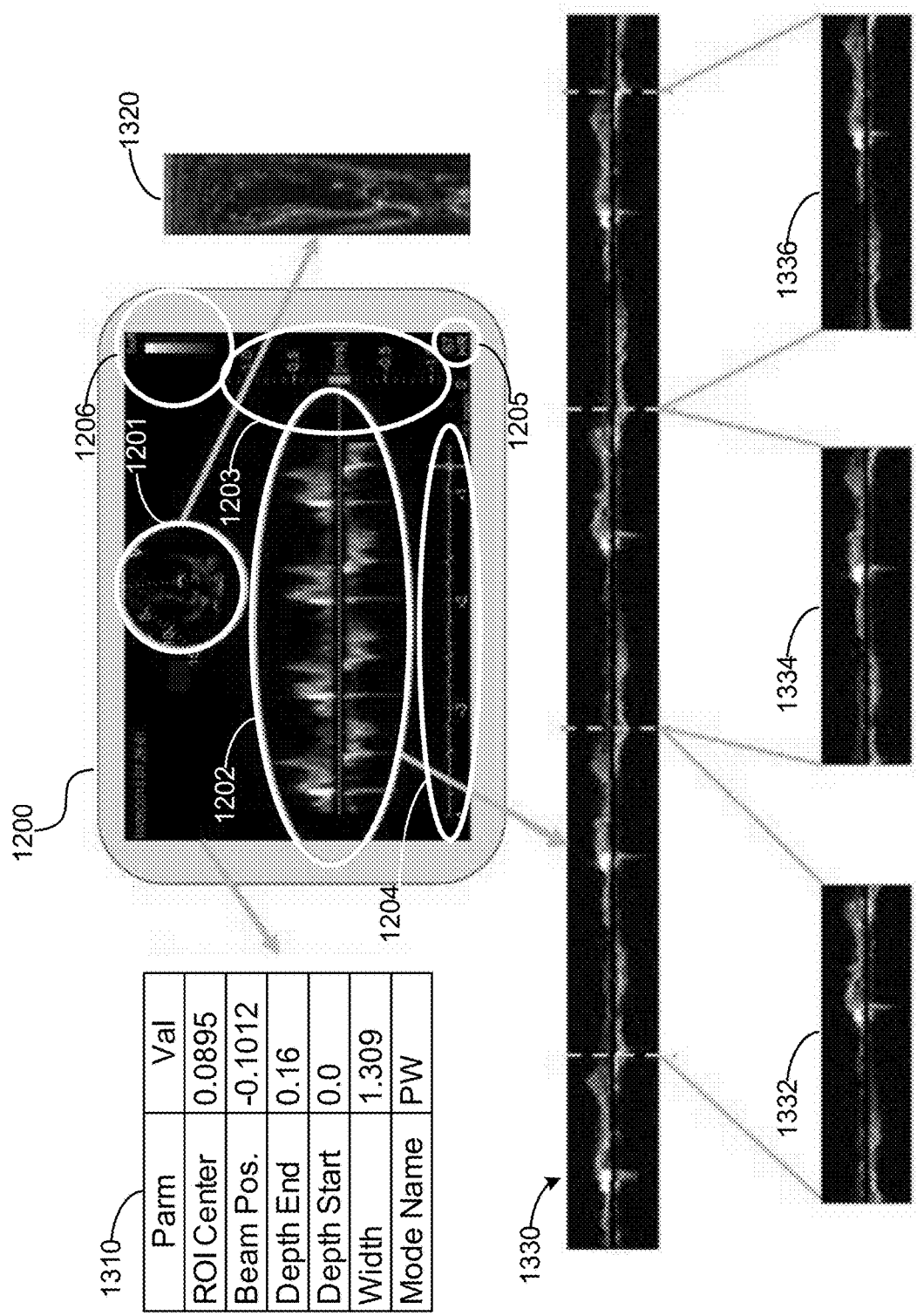
FIG. 13 shows an example of input data and associated output provided with respect to the ultrasound imaging device for imaging study classification analysis.

FIG. 13 shows an example of input data and associated output 1300 provided with respect to the device 1200 for imaging study classification analysis. As shown in the example of FIG. 13, parameters 1310 for an ultrasound Doppler scan can be extracted, as well as a B-Mode image 1320 as a raw, non-transformed image data array. A Doppler spectrum 1330 is segmented into heart cycles 1332, 1334, 1336, which are captured and cut into segments 1332-1336 via the ECG device attached to the patient, for example.

Figure 14:
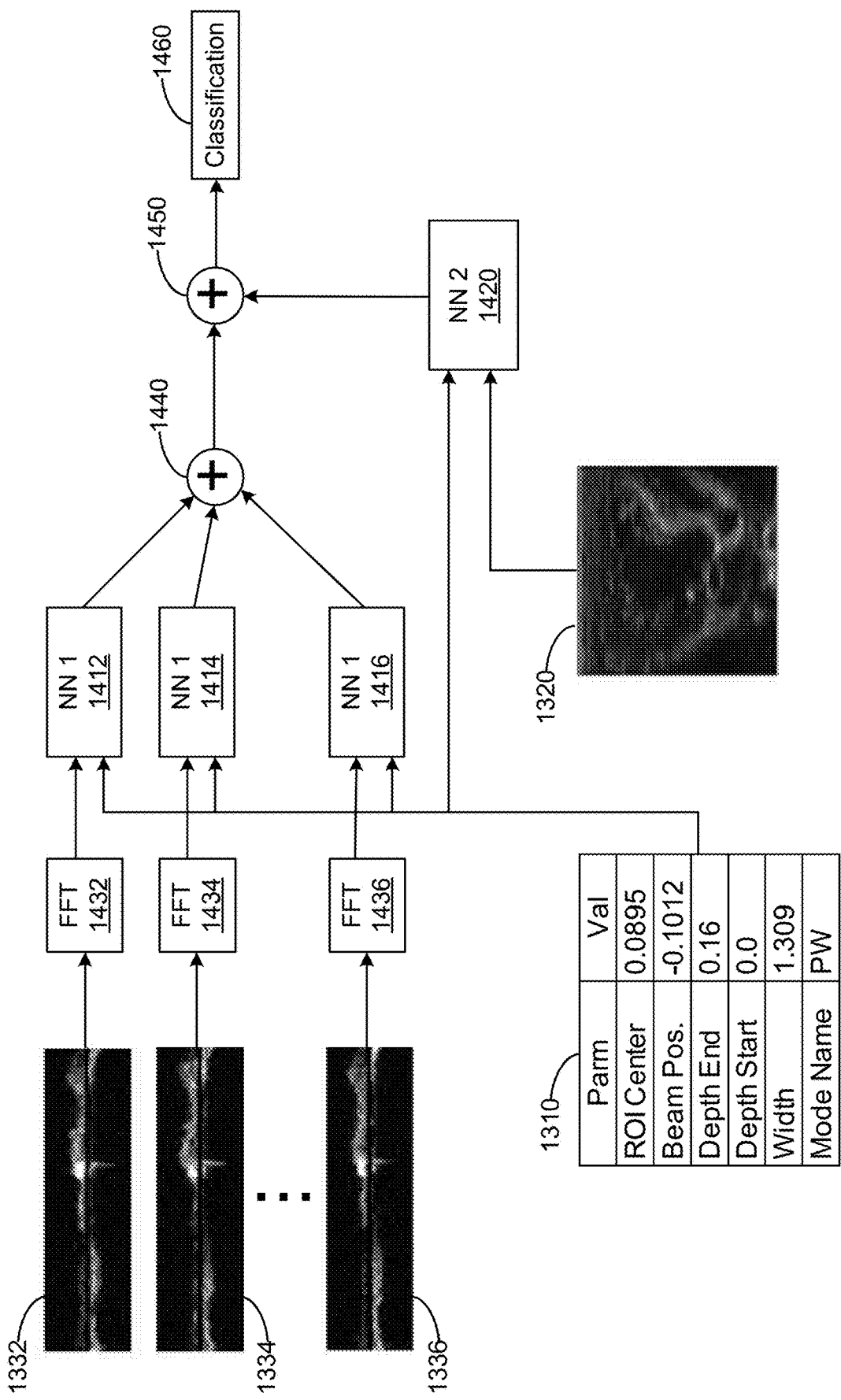
FIG. 14 shows an example classification system to classify an imaging study type.

In certain examples, an imaging study type is classified using an example classification system 1400 as shown in FIG. 14. The example classification system 1400 includes a plurality of first-type neural networks 1412-1416, which classify a study type based on data from a given heart cycle spectrogram plus the ultrasound parameters (network "NN1" 1412-12416). The example classification system includes a second-type neural network 1420, which classifies a study type based on the B-Mode image plus the (same) ultrasound parameters (network "NN2" 1420).

Each heart cycle spectrogram 1332-1336 is first processed by a 2D Fast Fourier Transform (FFT) procedure or filter 1432-1436. Then, a plurality of (e.g., 741, etc.) low-frequency 2D FFT coefficients are selected and their absolute values are computed by the FFT filters 1432-4436. These coefficient values are then used as input to the first-type neural networks NN1 1412-1416. Using FFT transforms a variable-size spectrogram 1332-1336 into a fixed (e.g., 741, etc.) number of values to be used as input for the neural network NN1 1412-1416. Thus, rather than resizing variable-size images, spectrogram 1332-1336 information is converted into FFT output coefficient values. For example, using FFT and low-frequency coefficient selection yields improved results over resizing of the images. The FFT can compress an image's energy into a compact representation, thereby preserving more information than a resized version of the image, for example.

In other examples, an image can be resized, rather than computing the FFT for the spectrum. Thus, a fixed-size input can be obtained by filtering via the FFT and/or by resizing the available image data, for example.

In certain examples, 2D-FFT coefficients (e.g., 741 2D-FFT coefficients, etc.) are generated by:

$$I[-L+1:,-L+1:] \text{ and } I[-L+1:,0:L]$$ (Eq. 3), where I denotes the 2D-FFT transformed matrix and L=20. The above expressions of Eq. (3) follow the Python Numpy-array indexing convention (e.g., [−M:] refers to the last M values of the array).

The FFT coefficient values computed by the FFT filters 1432-1436 for each heart cycle are combined with the input parameters 1310 to form an input for the neural network NN1 1412-1416. The network output of the NN1s 1412-1416 for each heart cycle is a distribution of probabilities for each available class of study (e.g., 10 classes, 13 classes such as AR, AVO, LVOT, MR, MVI, PVO, PulmVein, RVOT, LAT, SEP, RV, TR, TVI, etc., 14 classes, 15 classes, etc.). That is, the output is a list of values corresponding to the number of possible study classes (e.g., 10, 13, 14, 15, etc.), and the sum of those values is equal to 1. The maximum value of the output indicates the most likely class of the Doppler ultrasound study.

The NN1 1412-1416 FFT input and parameter 1310 analysis is performed for each heart cycle spectrogram 1332-1336. The number of available heart cycles is variable, so a number of times the NN1 1412-1416 analysis is repeated cannot be determined in advance for a given study. The distributions obtained by each heart cycle are averaged 1440, yielding one 13-value distribution that provides the study class type probabilities for the whole given spectrum 1330.

In parallel, the second neural network NN2 1420 computes another multi-value distribution (e.g., 10 values, 13 values, 14 values, 15 values, etc., corresponding to a number of possible classes) based on the B-Mode image 1320 and the parameters 1310. NN2 1420 is applied once per study, utilizing one B-Mode frame 1320. Prior to being input into the network NN2 1420, the B-Mode image 1320 is resized (e.g., to 32×32 pixels, etc.). The list of parameters 1310 is the same set of parameters 1310 used as input to the networks NN1 1412-1416.

An average distribution from the NN1 network instances 1412-1416 is then linearly combined 1450 with the distribution output from the network instance NN2 1420. The combination 1450 can be weighted to a total of 1, such as using a combination weight of ⅔ for the spectrum-based distribution and ⅓ for the B-Mode-based distribution, weights split ½ and ½ between the spectrum-based distribution and the B-Mode-based distribution, etc. The combiner 1450 provides the weighted combination of values to a classifier 1460 for classification of the type of Doppler ultrasound study being/to be performed.

In certain examples, the neural networks N1 1412-1416 and N2 1420 are trained using tagged Doppler study data, each assigned to one of the available study classes (e.g., 10, 13, 14, 15, etc.), along with heart cycle spectrograms. The tagged study data is divided into two groups: training studies (e.g., ~80%) and validation studies (e.g., ~20%).

To train the NN1 networks 1412-1416, a heart-cycle+parameter dataset is created. Each row of this dataset relates to one heart cycle and includes a fixed-sized input (e.g., FFT coefficient values (e.g., the 481 FFT values, etc.), etc.) concatenated with the N parameter features (e.g., 13 parameter features, 14 features, etc.) and a class tag. In certain examples, heart cycle records corresponding to a given study have the same N ultrasound feature parameters.

In certain examples, NN1 networks 1412-1416 are four-layer, densely connected neural network models including first and second hidden layers. In some examples, the first and second hidden layers include 50 and 25 nodes respectively. In certain examples, an activation function is the sigmoid for all neurons, and the output layer is a 13-long softmax layer.

The heart-cycle+parameter records associated with training studies are used for training, and the remaining records are used for validation. Thus, heart cycles of a given study are used for either training or validation, but not for both.

For NN2 1420, a B-Mode+parameter dataset is created, where each row relates to one image study. The inputs of each row are the pixels (e.g., 32×32 pixels, etc., flattened into one vector, not flattened, etc.) of the downscaled B-Mode frame 1320, concatenated with the parameter features (e.g., 13 parameter features, 14, 15, etc.) 1310 used with respect to NN1 1412-1416, as well as the class tag. The model for NN2 1420 is similar to the model of NN1 1412-1416, with the same number of layers and nodes in the hidden layers, and the same output layer. As with NN1 1412-1416, the rows associated with the training studies are used for training, and the remaining rows are used for validation.

FIG. 15 shows a table 1500 of example Doppler study classification results on test data. As shown in the example table 1500, an actual value 1510 for a study type can be compared to a predicted value 1520 for the study type. An accuracy of the example of FIG. 15 can be determined by computing a sum of the diagonal divided by an overall sum for a result of 460/485=94.85%. Thus, the final Doppler ultrasound study type classification performed by the system of FIG. 14 provides an accuracy of 94.85%.

Thus, if a patient is to be scanned according to one of the plurality (e.g., 13, etc.) of study categories or types, an ultrasound device is configured according to parameters associated with that study category (e.g., device settings, scan mode (e.g., PW, CW, etc.), etc.). The ultrasound probe is then positioned with respect to the patient to obtain the B-Mode image 1320. The probe can be adjusted to focus on the aorta, mitral valve, and/or other anatomy to be scanned (e.g., to look at aortic regurgitation, etc.). Thus, the B-Mode image 1320 is a reference for a user to specify where the Doppler scan is to occur (e.g., at a particular position within the heart, etc.). Coordinates (e.g., <x, y, z> coordinates, etc.) provide an indication of focus and can be used by the neural networks 1412-1420 to determine an anatomy of focus and extrapolate a classification or categorization of the Doppler study based on the anatomy of focus and parameters 1310, etc.

In Doppler mode, the scan procedure is frozen to obtain the spectrogram 1330 with time as the x axis such that the spectrogram 1330 is viewed over time in the Doppler scan. ECG data can be captured as well. As the patient is scanned, the spectra is synchronized with the ECG readout and moves as time moves to the right. Once information has been obtained, the scan be frozen or otherwise ended to process the data, for example.

Manual measurement of captured data (e.g., measure height of peaks, compute area under curve, etc.) can take minutes, while automated measurement via computer and/or other processor can be completed in seconds. However, for the system to know which algorithm to apply to measure and process the data, the system must know the intention or type of scan because different scans/goals/intentions are associated with different processing algorithms and/or different parameters to configure the processing algorithms. Otherwise, the automated algorithms are incapable of processing the information to achieve a meaningful, usable result. Thus, certain examples infer intention (e.g., study type, classification, category, etc.) to automatically select and apply the appropriate algorithm and/or parameter(s) for the algorithm to generate a usable output.

While example implementations are illustrated in conjunction with FIGS. 1-15, elements, processes and/or devices illustrated in conjunction with FIGS. 1-15 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 16:
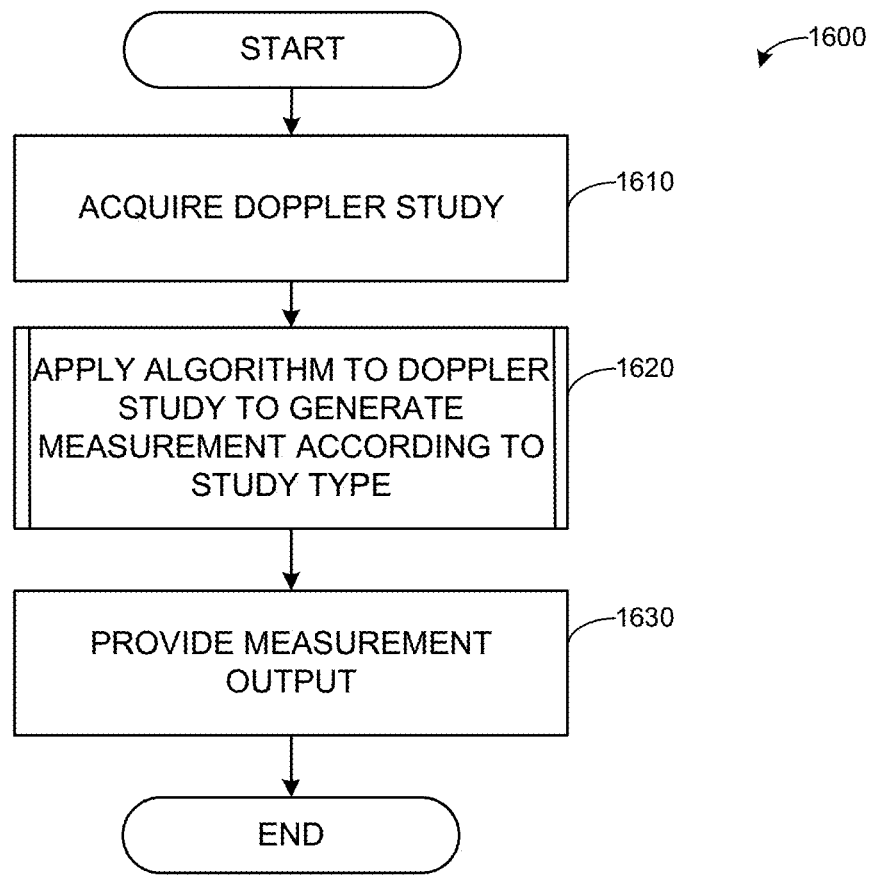
FIGS. 16-18 illustrate flow diagrams of example methods for Doppler image study classification.
Figure 17:
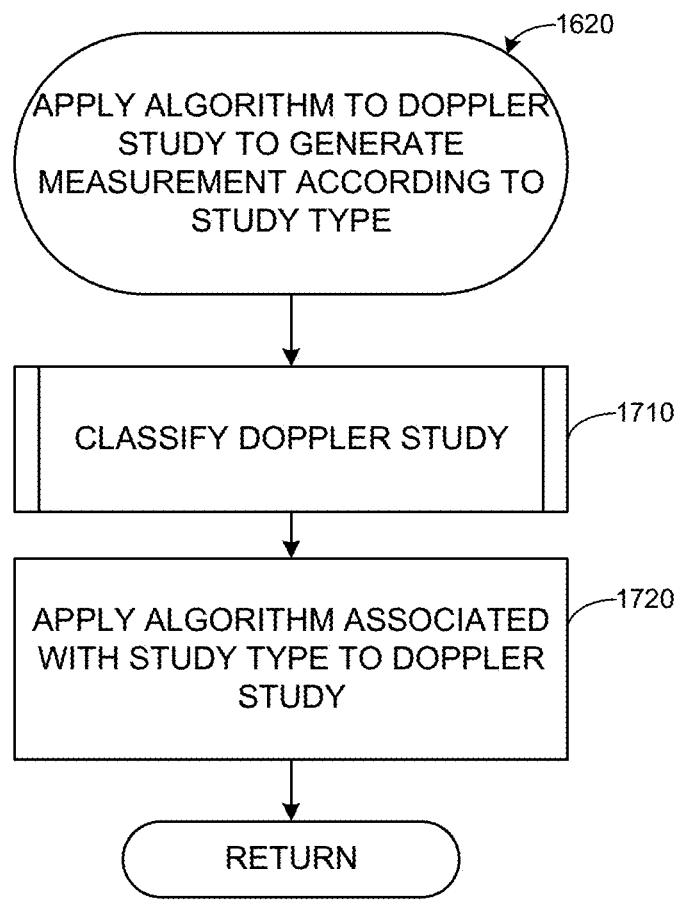
Figure 18:
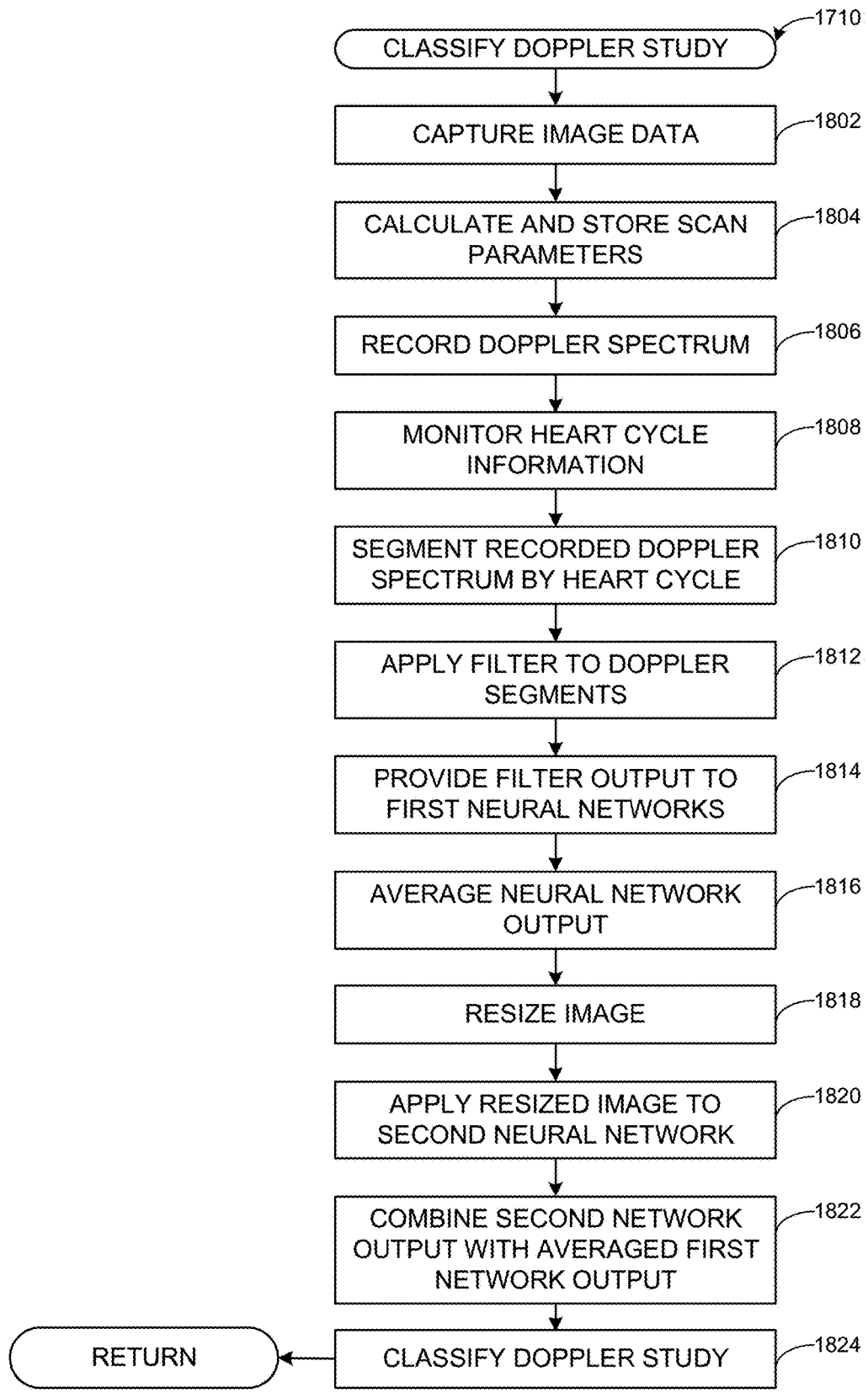

Flowcharts representative of example machine readable instructions for implementing components disclosed and described herein are shown in conjunction with at least FIGS. 16-18. In the examples, the machine readable instructions include a program for execution by a processor such as the processor 1912 shown in the example processor platform 1900 discussed below in connection with FIG. 19. The program may be embodied in machine readable instructions stored on a tangible computer readable storage medium such as a CD-ROM, a floppy disk, a hard drive, a digital versatile disk (DVD), a Blu-ray disk, or a memory associated with the processor 1912, but the entire program and/or parts thereof could alternatively be executed by a device other than the processor 1912 and/or embodied in firmware or dedicated hardware. Further, although the example program is described with reference to the flowcharts illustrated in conjunction with at least FIGS. 16-18, many other methods of implementing the components disclosed and described herein may alternatively be used. For example, the order of execution of the blocks may be changed, and/or some of the blocks described may be changed, eliminated, or combined. Although the flowcharts of at least FIGS. 16-18 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 16 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIGS. 16-18 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 1600 depicted in FIG. 16, an ultrasound Doppler study is acquired and processed. At block 1610, a Doppler study is acquired. For example, the ultrasound probe 110 is positioned with respect to a target, and the example exam classifier 1060

At block 1620, an algorithm and/or model is applied to the Doppler study to generate measurement output according to a type of the Doppler study. For example, based on the study type, a particular algorithm and/or model is applied to the Doppler spectrum scan data to generate a measurement of the scanned Doppler spectrum.

At block 1630, measurement output from the algorithm and/or model processing of the Doppler scan data is provided. For example, the measurement output can be displayed, reported, stored, transmitted to another clinical system for processing, etc.

FIG. 17 provides further detail regarding processing the Doppler study using an algorithm and/or model (block 1620 of the example of FIG. 16). At block 1710, the Doppler study is classified. For example, the study can be classified according to type (e.g., mitral value, TVI, etc.) and/or pathology (e.g., severe mitral regurgitation, etc.). At block 1720, an algorithm and/or model associated with the Doppler spectrum type is applied to the scanned Doppler spectrum. For example, a blood flow analysis algorithm and/or model can be applied to a cardiac Doppler study type. Point and/or beam direction information and movement velocity can be generated for a tissue (B-Mode) type ultrasound scan, for example. An E/A peak ratio can be computed and/or an area under an envelope trace can be calculated depending on scan type, for example.

FIG. 18 provides further detail regarding classifying the Doppler study (block 1710 of the example of FIG. 17). At block 1802, image data is captured. For example, one or more 2D and/or B-Mode images are captured by the imaging device 100 and relayed to the image capturer 1062. At block 1804, scan parameters are calculated and stored. Some scan parameters can be obtained from the imaging device 100 (e.g., scan depth, focus tilt, focus depth, aperture, baseline position, velocity interval, ultrasound mode, etc.), and others are calculated by the parameter calculator 106 (e.g., gate coordinates (x,y), etc.). Parameters can be stored in the parameter data store 1064, for example.

At block 1806, Doppler spectrum data is recorded. For example, Doppler spectrum information is captured by the imaging device 100 and relayed to the Doppler spectrum recorder 1070. At block 1808, heart cycle information for the target is monitored. For example, the heart cycle monitor 1068 receives ECG data indicative of the target's heart cycles. At block 1810, the recorded Doppler spectrum can be segmented according to the monitored heart cycles. For example, the Doppler spectrum can be divided into segments, each segment corresponding to a heart cycle for the target.

At block 1812, filters are applied to the segments of Doppler spectrum data. For example, the FFT 1432-1436 are applied to corresponding segments 1332-1336 of the scanned Doppler spectrum information. At block 1814, filter output is provided to a first set of neural networks (NN1) 1412-1416. The first set of neural networks 1412-1416 processes output from the FFT 1432-1436 to generate a probability of membership in each available study classification. For example, the neural networks 1412-1416 process the filtered Doppler segment data along with parameters 1310 to determine a probability that each segment belongs to one of thirteen possible categorizes or classifications of exam type. Thus, an output from each of the neural networks 1412-1416 is a set of probabilities that the given segment 1332-1336 resides in each possible class. The neural network analysis is completed for all Doppler segments available (e.g., which can vary depending on the study). The greatest probability (e.g., the highest value in the set of 13 possible classification values, etc.) indicates the most likely classification for the study.

At block 1816, the output of the set of first neural networks is averaged. For example, each segment 1332-1336 has a set of 13 classification probability values. The corresponding values can be averaged to form a set of 13 classification probability values for the entire Doppler scan.

At block 1818, the image (e.g., the 2D and/or B-Mode image) is resized. For example, the image can be resized to 32×32 pixels. At block 1820, the resized image is applied to a second neural network (NN2) 1420. For example, the neural network 1420 processes the resized image 1320 along with parameters 1310 to determine a probability that the image 1320 belongs to one of thirteen possible categorizes or classifications of exam type. Thus, an output from the neural network 1420 is a set of probabilities that the image 1320 resides in each possible class. The greatest probability (e.g., the highest value in the set of 13 possible classification values, etc.) indicates the most likely classification for the study.

At block 1822, the output of the second neural network 1420 is combined with the averaged output of the first set of neural networks 1412-1416. For example, the average distribution from networks NN1 1412-16 is linearly combined with the distribution output from network NN2 1420. In certain examples, combination weights are set to be ⅔ for the spectrum-based distribution from NN1 and ⅓ from the B-Mode-based distribution from NN2. At block 1824, the Doppler study type is classified based on the combination of the output of NN1 and NN2. For example, after combination, a highest probability class of the 13 possible classes is the most likely classification of the imaging study. The study is inferred to be of that class for automated selection of an algorithm/model and processing of the study data. Thus, while current systems and methods are unable to automate the image data processing because only a human can manually input the study type, certain examples overcome this technical problem by processing image and parameter information using a plurality of neural networks to infer the study type to automate processing of the image data, for example.

While some examples have been shown and described with respect to ultrasound images, the same systems and methods can be applied to MR, x-ray, MICT, CT, etc. In some examples, modalities can be combined such as applying a CT model to MR images, etc.

Figure 19:
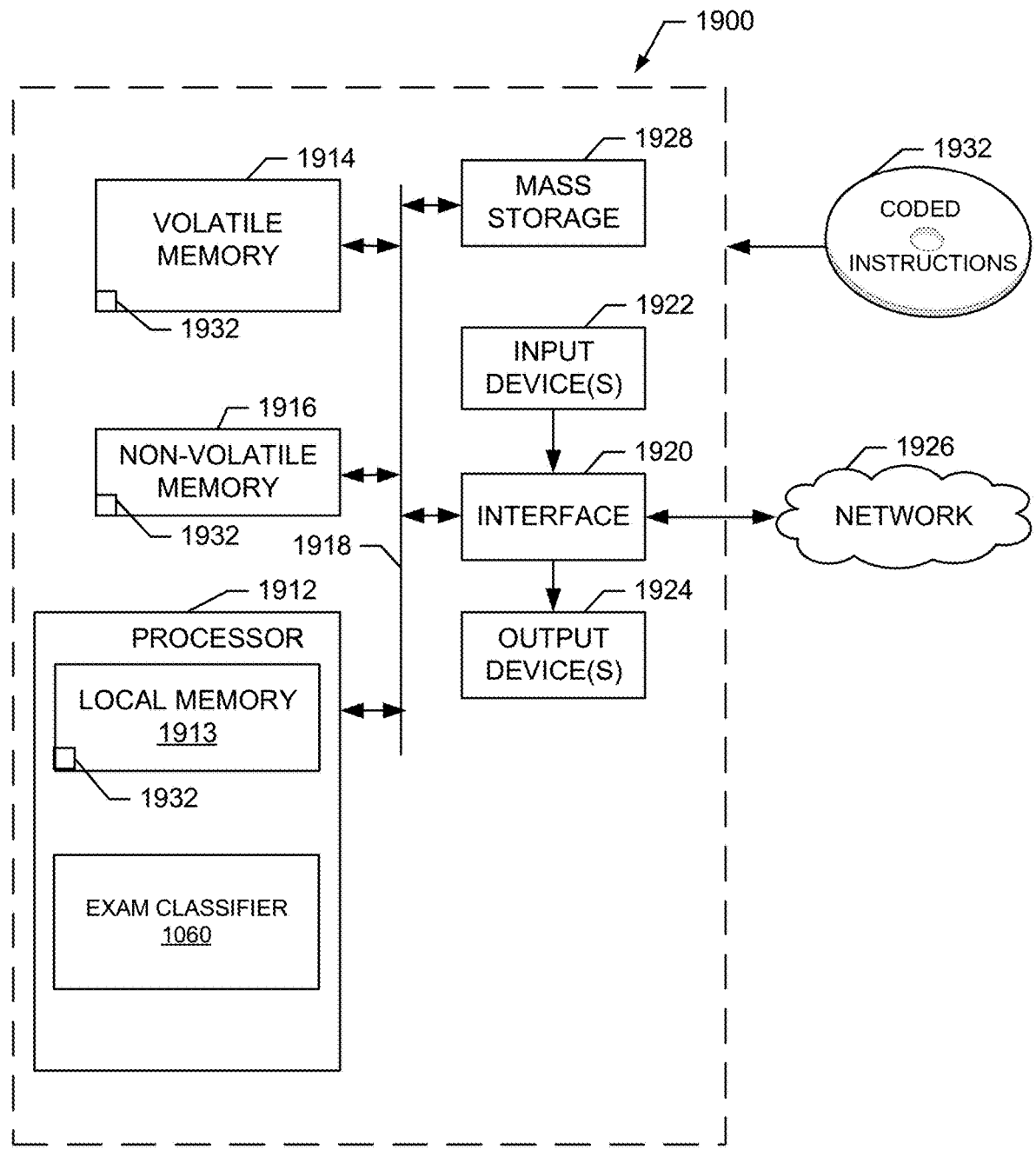
FIG. 19 is a block diagram of a processor platform structured to execute the example machine readable instructions to implement components disclosed and described herein.

FIG. 19 is a block diagram of an example processor platform 1900 structured to executing the instructions of at least FIGS. 16-18 to implement the example components disclosed and described herein. The processor platform 1900 can be, for example, a server, a personal computer, a mobile device (e.g., a cell phone, a smart phone, a tablet such as an iPad™), a personal digital assistant (PDA), an Internet appliance, or any other type of computing device.

The processor platform 1900 of the illustrated example includes a processor 1912. The processor 1912 of the illustrated example is hardware. For example, the processor 1912 can be implemented by integrated circuits, logic circuits, microprocessors or controllers from any desired family or manufacturer.

The processor 1912 of the illustrated example includes a local memory 1913 (e.g., a cache). The example processor 1912 of FIG. 19 executes the instructions of at least FIGS. 16-18 to implement the systems and infrastructure and associated methods of FIGS. 1-18 such as the example exam classifier 1060, etc. The processor 1912 of the illustrated example is in communication with a main memory including a volatile memory 1914 and a non-volatile memory 1916 via a bus 1918. The volatile memory 1914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1916 may be implemented by flash memory and/or any other desired type of memory device. Access to the main memory 1914, 1916 is controlled by a clock controller.

The processor platform 1900 of the illustrated example also includes an interface circuit 1920. The interface circuit 1920 may be implemented by any type of interface standard, such as an Ethernet interface, a universal serial bus (USB), and/or a PCI express interface.

In the illustrated example, one or more input devices 1922 are connected to the interface circuit 1920. The input device(s) 1922 permit(s) a user to enter data and commands into the processor 1912. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1924 are also connected to the interface circuit 1920 of the illustrated example. The output devices 1924 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1920 of the illustrated example, thus, typically includes a graphics driver card, a graphics driver chip or a graphics driver processor.

The interface circuit 1920 of the illustrated example also includes a communication device such as a transmitter, a receiver, a transceiver, a modem and/or network interface card to facilitate exchange of data with external machines (e.g., computing devices of any kind) via a network 1926 (e.g., an Ethernet connection, a digital subscriber line (DSL), a telephone line, coaxial cable, a cellular telephone system, etc.).

The processor platform 1900 of the illustrated example also includes one or more mass storage devices 1928 for storing software and/or data. Examples of such mass storage devices 1928 include floppy disk drives, hard drive disks, compact disk drives, Blu-ray disk drives, RAID systems, and digital versatile disk (DVD) drives.

The coded instructions 1932 of FIG. 19 may be stored in the mass storage device 1928, in the volatile memory 1914, in the non-volatile memory 1916, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A Doppler system comprising:
an image capturer to facilitate capture of a B-Mode image of a target as part of an ultrasound study;
a Doppler spectrum recorder to record a captured Doppler spectrum of the target from a Doppler gate position as part of the ultrasound study;
a study type inferrer including at least one neural network to process the B-mode image of the target and the Doppler gate position and to infer a study type of the ultrasound study based on the processing of the B-Mode image and the Doppler gate position, the study type inferred from a plurality of ultrasound study types; and
a processor to:
automatically select one or more measurements based on the study type inferred by the study type inferrer;
automatically perform the selected one or more measurements on the captured Doppler spectrum; and
at least one of: a) display the selected one or more measurements, b) report the selected one or more measurements, c) store the selected one or more measurements, or d) transmit the selected one or more measurements to a clinical system.

2. The system of claim 1, further including a parameter calculator to calculate gate coordinates indicating an anatomical position of the at least one of the two-dimensional ultrasound image or the B-Mode image.

3. The system of claim 2, wherein the parameter calculator is to calculate gate coordinates (x,y) by:

$$x = \frac{\langle\text{Focus Depth}\rangle - \langle\text{Min Scan Depth}\rangle}{\langle\text{Max Scan Depth}\rangle - \langle\text{Min Scan Depth}\rangle},$$

$$y = \frac{1}{2} + \frac{\langle\text{Focus Title}\rangle}{\langle\text{Aperture}\rangle}.$$

4. The system of claim 1, further including a heart cycle monitor to store the heart cycle of the target, the heart cycle to segment the captured Doppler spectrum into a plurality of Doppler segments, each Doppler segment to be processed using a set of neural networks.

5. The system of claim 4, further including a Fast Fourier Transform filter to filter the plurality of Doppler segments before the plurality of Doppler segments are processed by the set of neural networks.

6. The system of claim 4, wherein the processing the plurality of Doppler segments using the set of neural networks is to generate a plurality of first probability distributions, each of the plurality of first probability distributions corresponding to one of the plurality of Doppler segments, and wherein the plurality of first probability distributions is to be averaged to provide an average first probability distribution to be combined with the second probability distribution to infer the study type.

7. The system of claim 1, wherein the B-Mode image is to be resized before processing using the at least one neural network.

8. The system of claim 1, wherein the study type inferrer is to infer the study type by at least:
processing the Doppler spectrum using the at least one neural network to generate a first probability distribution among a plurality of study type classifications;
processing the B-Mode image using the at least one neural network to generate a second probability distribution among a plurality of study type classifications; and
combining the first probability distribution of study type classifications and the second probability distribution of study type classifications to infer the study type.

9. The system of claim 1, wherein the study type is one of: Aortic Regurgitation, Aortic Valve Out Flow, Left Ventricle Output Tract, Mitral Valve Regurgitation, Mitral Valve In Flow, Pulmonary Valve Out Flow, Pulmonary Vein, Right Ventricle Output Tract, Lateral Tissue Doppler In Flow, Septal Tissue Doppler In Flow, Right Ventricle Tissue Doppler In Flow, Tricuspid Valve Regurgitation, or Tricuspid Valve In Flow.

10. A non-transitory computer-readable storage medium including instructions which, when executed, cause at least one processor to at least:
process, using at least one neural network, a B-Mode image of a target and a Doppler gate position, the B-Mode image captured as part of an ultrasound study and the Doppler gate position used to capture a Doppler spectrum of the target as part of the ultrasound study;
infer a study type of the ultrasound study based on the processing, wherein the study type is inferred from a plurality of ultrasound study types;
automatically select one or more measurements based on the study type;
automatically perform the selected one or more measurement on the Doppler spectrum; and
at least one of a) display the selected one or more measurements, b) report the selected one or more measurements, c) store the selected one or more measurements, or d) transmit the selected one or more measurements to a clinical system.

11. The computer-readable storage medium of claim 10, wherein the instructions, when executed, cause the at least one processor to calculate gate coordinates indicating an anatomical position of the B-Mode image.

12. The computer-readable storage medium of claim 10, wherein the instructions, when executed, cause the at least one processor to segment the Doppler spectrum into a plurality of Doppler segments based on a heart cycle of the target.

13. The computer-readable storage medium of claim 12, wherein the instructions, when executed, cause the at least one processor to filter the plurality of Doppler segments using Fast Fourier Transforms.

14. The computer-readable storage medium of claim 12, wherein the instructions, when executed, cause the at least one processor to process the plurality of Doppler segments using the a least one neural network to generate a plurality of first probability distributions, each of the plurality of first probability distributions corresponding to one of the plurality of Doppler segments, and wherein the instructions, when executed, cause the at least one processor to average the plurality of first probability distributions to provide an average first probability distribution to be combined with the second probability distribution to infer study type.

15. The computer-readable storage medium of claim 10, wherein the instructions, when executed, cause the at least one processor to resize the B-Mode image before processing using the at least one neural network.

16. The computer-readable storage medium of claim 10, wherein the study type is one of: an Aortic Regurgitation, an Aortic Valve Out Flow, a Left Ventricle Output Tract, a Mitral Valve Regurgitation, a Mitral Valve In Flow, a Pulmonary Valve Out Flow, a Pulmonary Vein, a Right Ventricle Output Tract, a Lateral Tissue Doppler In Flow, a Septal Tissue Doppler In Flow, a Right Ventricle Tissue Doppler In Flow, a Tricuspid Valve Regurgitation, or a Tricuspid Valve In Flow.

17. A computer-implemented method comprising:
processing, using at least one processor and at least one neural network, a B-Mode image of a target and a Doppler gate position, the B-Mode image captured as part of an ultrasound study and the Doppler gate position used to capture a Doppler spectrum of the target as part of the ultrasound study;
inferring, using the at least one processor, a study type associated with the scanned Doppler spectrum of the ultrasound study based on the processing, wherein the study type is inferred from a plurality of ultrasound study types;
automatically selecting, using the at least one processor, one or more measurements based on the study type;
automatically performing, using the at least one processor, the selected one or more measurement on the Doppler spectrum; and
at least one of a) displaying the selected one or more measurements, b) reporting the selected one or more measurements, c) storing the selected one or more measurements, or d) transmitting the selected one or more measurements to a clinical system.

18. The method of claim 17, further including calculating gate coordinates indicating an anatomical position of the B-Mode image.

19. The method of claim 17, further including segmenting the Doppler spectrum into the plurality of Doppler segments based on a heart cycle of the target.

20. The method of claim 19, further including filtering the plurality of Doppler segments using Fast Fourier Transforms.

21. The method of claim 19, further including:
processing the plurality of Doppler segments using the at least one neural network to generate a plurality of first probability distributions, each of the plurality of first probability distributions corresponding to one of the plurality of Doppler segments; and
averaging the plurality of first probability distributions to provide an average first probability distribution to be combined with the second probability distribution to infer the study type.

22. The method of claim 17, further including resizing the B-Mode image before processing using the at least one neural network.

23. The method of claim 19, further including facilitating application of at least one of a processing algorithm or a model to the Doppler spectrum formed of the plurality of Doppler segments based on the study type.

24. The method of claim 17, wherein the study type is one of an Aortic Regurgitation, an Aortic Valve Out Flow, a Left Ventricle Output Tract, a Mitral Valve Regurgitation, a Mitral Valve In Flow, a Pulmonary Valve Out Flow, a Pulmonary Vein, a Right Ventricle Output Tract, a Lateral Tissue Doppler In Flow, a Septal Tissue Doppler In Flow, a Right Ventricle Tissue Doppler In Flow, a Tricuspid Valve Regurgitation, or a Tricuspid Valve In Flow.

* * * * *